(12) United States Patent  
Clark et al.

(10) Patent No.: US 7,294,623 B2
(45) Date of Patent: Nov. 13, 2007

(54) BENZYL MORPHOLINE DERIVATIVES

(75) Inventors: Barry Peter Clark, Basingstoke (GB); Peter Thaddeus Gallagher, Basingstoke (GB); Helen Louise Haughton, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 332 days.

(21) Appl. No.: 10/524,798

(22) PCT Filed: Aug. 18, 2003

(86) PCT No.: PCT/US03/23268

§ 371 (c)(1),
(2), (4) Date: Feb. 17, 2005

(87) PCT Pub. No.: WO2004/018440

PCT Pub. Date: Mar. 4, 2004

(65) Prior Publication Data

US 2006/0052377 A1    Mar. 9, 2006

Related U.S. Application Data

(60) Provisional application No. 60/415,327, filed on Oct. 1, 2002.

(30) Foreign Application Priority Data

Aug. 23, 2002 (GB) .................. 0219685.5

(51) Int. Cl.
*A61K 31/5375* (2006.01)
*C07D 265/30* (2006.01)

(52) U.S. Cl. .................. 514/239.2; 544/158

(58) Field of Classification Search ........... 544/158; 514/239.2
See application file for complete search history.

(56) References Cited

U.S. PATENT DOCUMENTS

| 4,956,388 A | 9/1990 | Robertson et al. |
| 5,023,269 A | 6/1991 | Robertson et al. |

FOREIGN PATENT DOCUMENTS

| GB | 1295447 A | 11/1972 |
| GB | 1412546 A | 11/1975 |
| GB | 2167407 A | 5/1986 |
| WO | WO-99-15177 | 4/1999 |
| WO | WO-00-39091 | 7/2000 |
| WO | WO-01-01973 A2 | 1/2001 |
| WO | WO-2004-017977 A2 | 3/2004 |

*Primary Examiner*—Rebecca Anderson
(74) *Attorney, Agent, or Firm*—Robert D. Titus; Arvie J. Anderson

(57) ABSTRACT

A compound of formula (I) (I) wherein R is H; Ar is an aromatic group selected from phenyl; X is a phenyl group; R' is H or C1-C4 alkyl; each R1 is independently H or C1-C4 alkyl; and pharmaceutically acceptable salts thereof

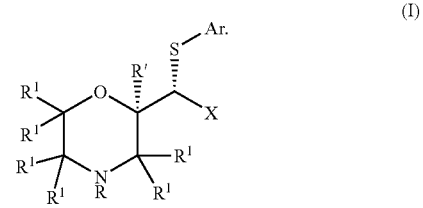

(I)

7 Claims, No Drawings

BENZYL MORPHOLINE DERIVATIVES

This is the national phase application, under 35 USC 371, for PCT/US2003/023268, filed 1 Aug. 2003, which claims the benefit, under 35 USC 119(e), of U.S. provisional application No. 60/415,327, filed 1 Oct. 2002 and, under 35 USC 119(a), of GB application 0219685.5, filed 23 Aug. 2002.

This invention relates to novel benzyl morpholine compounds, and to their use in inhibiting serotonin and norepinephrine reuptake.

Serotonin has been implicated in the aetiology of many disease states and has been found to be of importance in mental illnesses, depression, anxiety, schizophrenia, eating disorders, obsessive compulsive disorder (OCD) and migraine. Indeed many currently used treatments of these disorders are thought to act by modulating serotonergic tone. During the last decade, multiple serotonin receptor subtypes have been characterised. This has led to the realisation that many treatments act via the serotonergic system, such as selective serotonin reuptake inhibitor (SSRI) antidepressants which increase serotonin transmission, for example, the hydrochloride salt of fluoxetine.

Drugs that exert their main action on the norepinephrinergic system have been available for some time, however their lack of selectivity has made it difficult to determine specific clinical effects produced by a selective action on norepinephrine reuptake. Accumulating evidence indicates that the norepinephrinergic system modulates drive and energy, whereas the serotonergic system modulates mood. Thus norepinephrine appears to play an important role in the disturbances of vegetative function associated with affective, anxiety and cognitive disorders. Atomoxetine hydrochloride is a selective inhibitor of norepinephrine reuptake, and is marketed for the treatment of attention deficit hyperactivity disorder (ADHD). Reboxetine is also a selective norepinephrine reuptake inhibitor and is marketed for the treatment of depression. WO99/15177 discloses the use of Reboxetine to treat ADHD and WO01/01973 discloses the use of S,S-Reboxetine to treat ADHD.

Norepinephrine and serotonin receptors are known to interact anatomically and pharmacologically. Compounds that affect only serotonin have been shown to exhibit modulatory effects on norepinephrine, pointing toward an important relationship between the two neurotransmitter systems.

Duloxetine, (+)-N-methyl-3-(1-naphthalenyloxy)-2-thiophenepropanamine hydrochloride, inhibits the reuptake of both norepinephrine and serotonin, and is currently under development for the treatment of depression and urinary incontinence. The compound duloxetine was disclosed in U.S. Pat. Nos. 5,023,269 and 4,956,388.

According to the present invention there is provided a compound of formula (I)

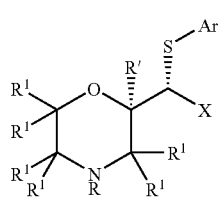

wherein
R is H;

Ar is an aromatic group selected from phenyl; X is a phenyl group; R' is H or $C_1$-$C_4$ alkyl; and each $R_1$ is independently H or $C_1$-$C_4$ alkyl; and pharmaceutically acceptable salts thereof.

The aromatic group Ar may be substituted or unsubstituted phenyl. For example, Ar may be unsubstituted phenyl or, preferably, phenyl substituted with 1, 2, 3, 4 or 5 substitutents, preferably with 1 or 2, for example 1, substituent. The substituted phenyl group is preferably substituted in the 2-position. Suitable substitutents include $C_1$-$C_4$ alkyl, $O(C_1$-$C_4$ alkyl), $S(C_1$-$C_4$ alkyl), halo, and phenyl, optionally substituted with, for example, halo, $C_1$-$C_4$ alkyl or $O(C_1$-$C_4$ alkyl).

The group X may be substituted or unsubstituted phenyl. For example, X may be phenyl substituted with 1, 2, 3, 4 or 5 substituents, preferably with 1 substituent. Suitable substituents include $C_1$-$C_4$ alkyl, $O(C_1$-$C_4$ alkyl), and halo.

"$C_1$-$C_4$ alkyl" as used herein includes straight and branched chain alkyl groups of 1, 2, 3 or 4 carbon atoms, and may be unsubstituted or substituted. $C_1$-$C_2$ alkyl groups are preferred. Suitable substituents include halo. Thus the term "$C_1$-$C_4$ alkyl" includes haloalkyl. Similar terms defining different numbers of C atoms (e.g. "$C_1$-$C_2$ alkyl") take an analogous meaning. When R' is $C_1$-$C_4$ alkyl it is preferably unsubstituted. When $R^1$ is $C_1$-$C_4$ alkyl it is preferably unsubstituted.

"Halo" includes F, Cl, Br and I, and is preferably F or Cl.

For the compounds of formula (I) above, R' is preferably H or Me. More preferably R' is H.

For the compounds of formula (I) above, each $R^1$ is preferably H or Me with 0, 1, 2 or 3 of $R^1$ being Me. More preferably only 1 $R^1$ is Me. Most preferably all $R^1$ are H.

For the compounds of formula (I) above, it is preferred that R' and all $R^1$ are H.

Particularly preferred substituents for the Ar group include trifluoromethyl and methoxy.

A preferred group of compounds according to the present invention is represented by formula (II);

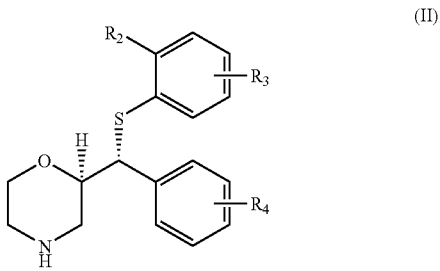

in which $R_2$ and $R_3$ are each independently selected from H, $C_1$-$C_4$ alkyl, $O(C_1$-$C_4$ alkyl), $S(C_1$-$C_4$ alkyl), halo, and phenyl; and $R_4$ is selected from H, $C_1$-$C_4$ alkyl, and $O(C_1$-$C_4$ alkyl) and halo; and pharmaceutically acceptable salts thereof.

$R_2$ is preferably $C_1$-$C_2$ alkyl, $O(C_1$-$C_2$ alkyl), $S(C_1$-$C_2$ alkyl), Cl or F. $R_3$ is preferably H, Me or Cl. $R_4$ is preferably H, $C_1$-$C_2$ alkyl, $O(C_1$-$C_2$ alkyl), Cl or F.

The compounds of the present invention are dual reuptake inhibitors of serotonin and norepinephrine. Biogenic amine transporters control the amount of biogenic amine neurotransmitters in the synaptic cleft. Inhibition of the respective transporter leads to a rise in the concentration of that neurotransmitter within the synaptic cleft. Compounds of Formula (I) and their pharmaceutically acceptable salts preferably exhibit a $K_i$ value less than 100 nM at the norepinephrine transporter and a $K_i$ value less than 100 nM at the serotonin transporter as determined using the scintillation proximity assays as described below. More preferred compounds of Formula (I) and their pharmaceutically acceptable salts exhibit a $K_i$ value less than 50 nM at the norepinephrine transporter and a $K_i$ value less than 50 nM at the serotonin transporter. Especially preferred compounds of Formula (I) and their pharmaceutically acceptable salts exhibit a $K_i$ value less than 20 nM at the norepinephrine transporter and a $K_i$ value less than 20 nM at the serotonin transporter. Preferably, compounds of the present invention selectively inhibit the norepinephrine and serotonin transporters relative to the dopamine transporter by a factor of at least five, more preferably by a factor of at least ten. Advantageously, they have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below. They are particularly useful for the treatment of disorders associated with serotonin and norepinephrine dysfunction in mammals, such as CNS disorders including depression, persistant pain and stress urinary incontinence.

The term "serotonin and norepinephrine dysfunction" as used herein refers to a reduction in the amount of serotonin and norepinephrine neurotransmitter within the synaptic cleft below that which would be considered to be normal. Thus the phrase "disorders associated with serotonin and norepinephrine dysfunction in mammals" refers to disorders which are associated with a reduction in the amount of serotonin and norepinephrine neurotransmitter within the synaptic cleft below that which would be considered to be normal for the mammalian species in question. Some examples of disorders currently believed to be associated with reduced levels of serotonin and norepinephrine within the synaptic cleft are detailed below.

The compounds of the present invention are also indicated for the treatment of disorders which are ameliorated by an increase in the amount of serotonin and norepinephrine neurotransmitter within the synaptic cleft of a mammal above that which would be considered to be normal for the mammalian species in question.

The term "treatment" as used herein refers to both curative and prophylactic treatment of disorders associated with serotonin and norepinephrine dysfunction.

Compounds of the present invention may be prepared by reacting a compound of the formula (III):

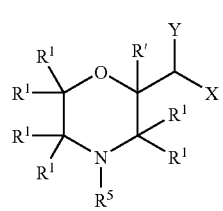

(III)

where R5 is a protecting group, e.g. benzyl, X, R' and $R^1$ are as formula I above and Y is a leaving group, with an aryl thiol. Examples of suitable leaving groups include halo and mesylate, but the nature of the leaving group is not critical.

Compounds of the present invention may also be prepared by deprotecting a compound of the formula (IV):

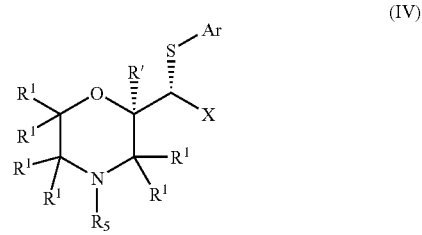

(IV)

where $R_5$ is a protecting group, e.g. benzyl, and Ar, X, R' and $R^1$ are as defined in formula (I) above to provide a compound of formula (I), optionally followed by the step of forming a pharmaceutically acceptable salt.

Suitable N-protecting groups will be known to the person skilled in the art as will methods for their removal. Further information on suitable deprotecting groups is contained in the well known text "Protective Groups in Organic Synthesis", Theodora W. Greene and Peter G. M. Wuts, John Wiley & Sons, Inc., New York, 1999, pp. 494-653. Preferred N-protecting groups include benzyl, allyl, carbamates such as benzyloxycarbonyl (cbz) and t-butyloxycarbonyl (boc) and amides.

Compounds of the present invention may be prepared by conventional organic chemistry techniques from N-benzyl-cyanomorpholine 1 (Route A) or N-benzyl-morpholinone 2 (Route B) as outlined in Scheme 1 below. For clarity, X is shown as phenyl and R' and $R^1$ are shown as H. It will be appreciated that analogous methods could be applied for other possible identities of X, R' and $R^1$.

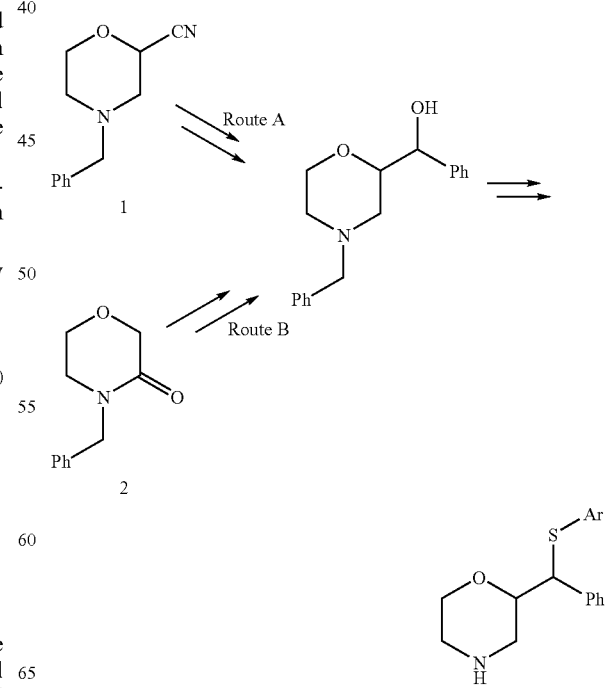

Scheme 1

More detail of Route A is given in Scheme 2:

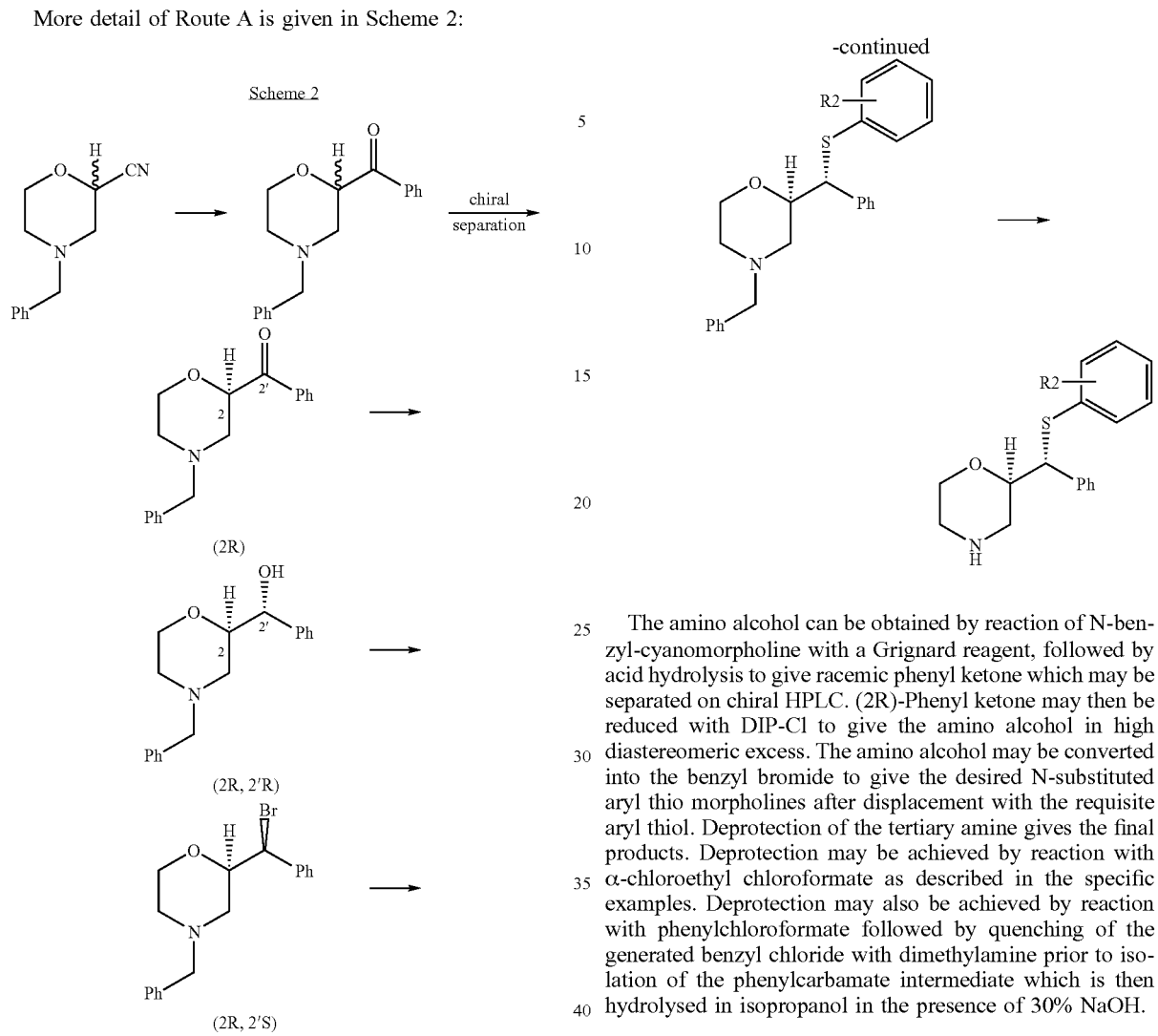

The amino alcohol can be obtained by reaction of N-benzyl-cyanomorpholine with a Grignard reagent, followed by acid hydrolysis to give racemic phenyl ketone which may be separated on chiral HPLC. (2R)-Phenyl ketone may then be reduced with DIP-Cl to give the amino alcohol in high diastereomeric excess. The amino alcohol may be converted into the benzyl bromide to give the desired N-substituted aryl thio morpholines after displacement with the requisite aryl thiol. Deprotection of the tertiary amine gives the final products. Deprotection may be achieved by reaction with α-chloroethyl chloroformate as described in the specific examples. Deprotection may also be achieved by reaction with phenylchloroformate followed by quenching of the generated benzyl chloride with dimethylamine prior to isolation of the phenylcarbamate intermediate which is then hydrolysed in isopropanol in the presence of 30% NaOH.

Detail of Route B is Given in Scheme 3:

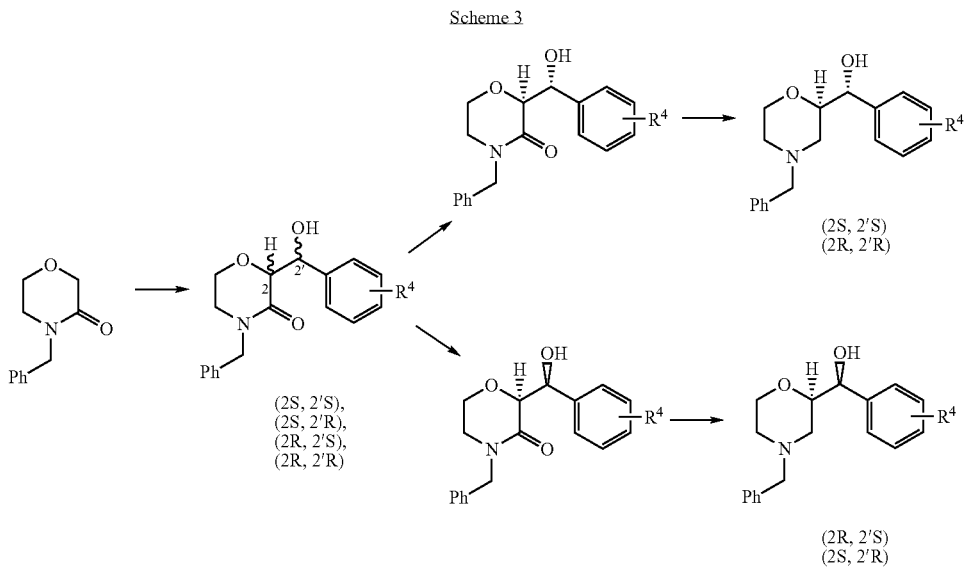

Treatment of N-benzyl morpholinone with a strong base such as lithium diisopropylamide at low temperature followed by addition of benzaldehyde gives aldol adducts as a 2:1 mixture of diastereomer pairs, which may be separated using conventional chromatographic techniques. Reduction with a borane reagent at elevated temperatures gives diasteremeric amino alcohol pairs.

Amino alcohol pair (2S,2'S) and (2R,2'R) may be converted to bromide and further to racemic aryl thio morpholines as outlined in Scheme 4. Amino alcohol pair (2R,2'S) and (2S,2'R) may be converted into the corresponding mesylate. Displacement with the requisite thiol, followed by removal of the nitrogen protecting group furnishes aryl thiol morpholines as racemic mixtures of two diastereomers. The racemic aryl thiol morpholines may be separated into enantiomerically pure products using chiral HPLC technology.

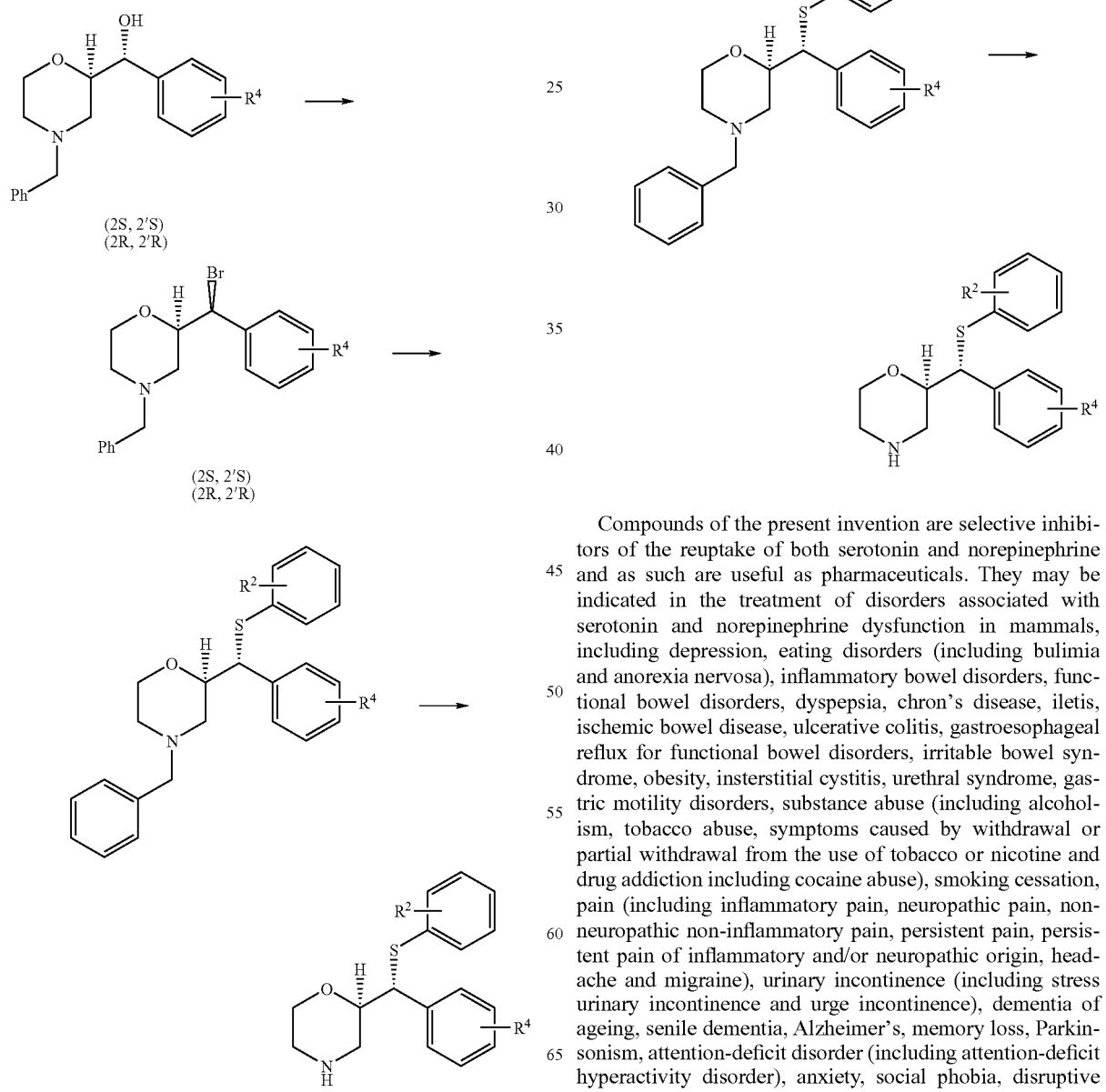

Compounds of the present invention are selective inhibitors of the reuptake of both serotonin and norepinephrine and as such are useful as pharmaceuticals. They may be indicated in the treatment of disorders associated with serotonin and norepinephrine dysfunction in mammals, including depression, eating disorders (including bulimia and anorexia nervosa), inflammatory bowel disorders, functional bowel disorders, dyspepsia, chron's disease, iletis, ischemic bowel disease, ulcerative colitis, gastroesophageal reflux for functional bowel disorders, irritable bowel syndrome, obesity, insterstitial cystitis, urethral syndrome, gastric motility disorders, substance abuse (including alcoholism, tobacco abuse, symptoms caused by withdrawal or partial withdrawal from the use of tobacco or nicotine and drug addiction including cocaine abuse), smoking cessation, pain (including inflammatory pain, neuropathic pain, non-neuropathic non-inflammatory pain, persistent pain, persistent pain of inflammatory and/or neuropathic origin, headache and migraine), urinary incontinence (including stress urinary incontinence and urge incontinence), dementia of ageing, senile dementia, Alzheimer's, memory loss, Parkinsonism, attention-deficit disorder (including attention-deficit hyperactivity disorder), anxiety, social phobia, disruptive behavior disorders, conduct disorders, impulsive control disorders, borderline personality disorder, chronic fatigue syndrome, panic disorders, obsessive compulsive disorder, post-traumatic stress disorder, schizophrenia, gastrointestinal disorders, cardiovascular disorders, emesis, sleep disorders, cognitive disorders, psychotic disorders, brain trauma, premenstrual syndrome or late luteal syndrome, sexual dysfunction (including premature ejaculation and erectile difficulty), autism, mutism and trichotilomania. The compounds of the present invention are particularly suitable for the treatment of pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and chronic pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

Current therapies for persistent pain include opiates, barbiturate-like drugs such as thiopental sodium and surgical procedures such as neurectomy, rhizotomy, cordotomy, and cordectomy.

References herein to pain are intended to refer to persistent pain.

The present invention provides pharmaceutical compositions comprising a compound of formula I or formula II or a pharmaceutically acceptable salt thereof, together with a pharmaceutically acceptable diluent or carrier.

Further, the present invention provides a compound of formula I or a pharmaceutically acceptable salt thereof, for use as a pharmaceutical; and a compound of formula I or a pharmaceutically acceptable salt thereof, for use as a selective inhibitor of the reuptake of both serotonin and norepinephrine. Preferably such selective inhibition occurs within mammalian cells (including mammalian cell membrane preparations), especially those found within the central and/or peripheral nervous system. More preferably such selective inhibition occurs within the cells of the central nervous system of a mammal, especially a human, in need thereof.

The present invention also provides the use of a compound of formula I or formula II, or a pharmaceutically acceptable salt thereof, in the manufacture of a medicament for selectively inhibiting the reuptake of serotonin and norepinephrine; the use of a compound of formula I or formula II, or a pharmaceutically acceptable salt thereof, in the manufacture of a medicament for the treatment of disorders associated with serotonin and norepinephrine dysfunction in mammals; the use of a compound of formula I or formula II, or a pharmaceutically acceptable salt thereof, in the manufacture of a medicament for the treatment of a disorder selected from depression, OCD, anxiety, memory loss, urinary incontinence, conduct disorders, ADHD, obesity, alcoholism, smoking cessation and pain; and the use of a compound of formula I or formula II, or a pharmaceutically acceptable salt thereof, in the manufacture of a medicament for the treatment of a disorder selected from depression, stress urinary incontinence, and persistent pain. The present invention further provides a compound of formula I or formula II for treating disorders associated with serotonin and norepinephrine dysfunction in mammals, for example a disorder selected from depression, OCD, anxiety, memory loss, urinary incontinence, conduct disorders, ADHD, obesity, alcoholism, smoking cessation and pain, especially depression, stress urinary incontinence, and persistent pain.

Further the present invention provides a method for selectively inhibiting the reuptake of serotonin and norepinephrine in mammals, comprising administering to a patient in need thereof an effective amount of a compound of formula I or formula II or a pharmaceutically acceptable salt thereof; a method for treating disorders associated with serotonin and norepinephrine dysfunction in mammals, comprising administering to a patient in need thereof an effective amount of a compound of formula I or formula II or a pharmaceutically acceptable salt thereof; and a method for treating a disorder selected from depression, OCD, anxiety, memory loss, urinary incontinence, conduct disorders, ADHD, obesity, alcoholism, smoking cessation and pain, especially depression, stress urinary incontinence or persistant pain, comprising administering to a patient in need thereof an effective amount of a compound of formula I or a pharmaceutically acceptable salt thereof.

The present invention includes the pharmaceutically acceptable salts of the compounds of formula I and formula II. Suitable salts include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, o-mandelic-1, mandelic-dl, mandelic d, maleic, mesotartaric monohydrate, hydroxymaleic, fumaric, lactobionic, malic, methanesulphonic, napsylic, naphthalenedisulfonic, naphtoic, oxalic, palmitic, phenylacetic, propionic, pyridyl hydroxy pyruvic, salicylic, stearic, succinic, sulfanilic, tartaric, 2-hydroxyethane sulphonic, toluene-p-sulphonic, and xinafoic acids.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

It will be appreciated that compounds of formula I and formula II possess one or more asymmetric carbon atoms, and that the present invention is directed specifically to individual stereoisomers. The particular stereochemistry of the present compounds is essential to the pharmacological profile of the compounds. In the present specification, where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent, excipient or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosols (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propyl- hydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a unit dosage form, each dosage unit containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

The following Examples illustrate compounds of the present invention and methods for their synthesis.

Stereochemical Conventions

The absolute stereochemistry of compounds according to the present invention may be determined by reference to X-ray crystallography for the following (2S,2'S) compound

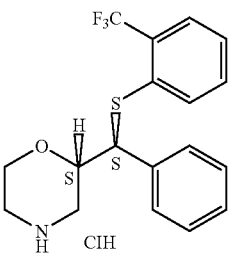

X-ray crystallographic data for the above compound is listed in Tables 1-6 herein.

All of the Examples herein were obtained as single isomers either through the use of chirally pure starting material or chiral separation methods, such as HPLC.

EXAMPLE 1

(2R)-2-((R)-[4-methoxyphenyl]{[2-methoxyphenyl]thio}methyl)morpholine hydrochloride i) (+/−)-[4-Methoxyphenyl][(4-benzylmorpholin-2-yl]methanone

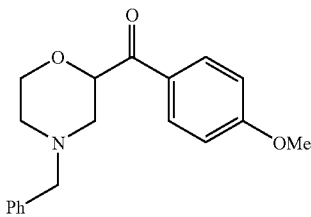

To stirred magnesium turnings (5.4 g, 0.22 mol) in dry THF (20 ml) at room temperature under nitrogen was added sufficient 1,2-dibromoethane (ca. 0.3 ml) to create an exotherm. A solution of 4-bromoanisole (13.90 g, 74.25 mmol) in dry THF (25 ml) was then added dropwise at a rate to maintain a gentle reflux. After addition, allowed to cool to below 30° C. then added over 5 min. period to a stirred solution of 4-benzyl-2-cyanomorpholine (5.0 g, 24.75 mmol) in dry THF (50 ml) cooled to −20° C. under nitrogen. After addition stirred at room temperature for 30 min. then cooled to 0° C. and added 5M HCl (25 ml) dropwise. After 5 min. stirring, made basic by addition of 2M NaOH and the resulting suspension filtered through celite. The aqueous phase was separated and washed with diethyl ether (2×). The combined organic phases was dried over magnesium sulphate, filtered and evaporated to a yellow oil. The oil was purified by flash chromatography on silica eluting with ethyl acetate/heptane gradient 25/75 to 70/30 to give required product as a yellow oil (5.46 g).

ii) (R)-[4-methoxyphenyl][(2S)-4-benzylmorpholin-2-yl]methanol and (S)-[4-methoxyphenyl][(2R)-4-benzylmorpholin-2-yl]methanol

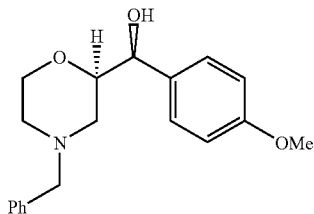

To a stirred solution of (+/−)-[4-Methoxyphenyl][4-benzylmorpholin-2-yl]methanone (5.40 g, 17.36 mmol) in methanol (60 ml) at 5° C. was added sodium borohydride (1.31 g, 34.72 mmol) portionwise. The mixture was stirred at room temperature for 1.5 h, cooled to 10° C. and added water to terminate reaction. Concentrated in vacuo, diluted with water and extracted with ethyl acetate (2×). Extracts washed with water and brine, dried over magnesium sulphate, filtered and evaporated to an oil. The crude mixture of diastereomers was purified and separated by flash chromatography on silica eluting with diethyl ether/toluene (3/2) to give the title diastereomer as a colourless oil (2.14 g).

iii) (2R)-2-((R)-[4-methoxyphenyl]{[2-methoxyphenyl]thio}methyl)-4-benzylymorpholine and (2S)-2-((S)-[4-metloxyphenyl]{[2-nethoxyphenyl]thio}methyl)-4-benzylmorpholine

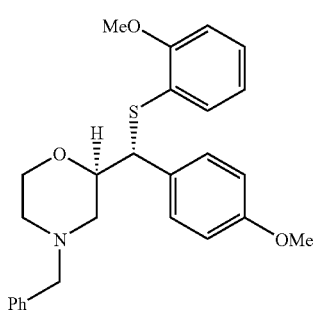

A mixture of (R)-[4-methoxyphenyl][(2S)-4-benzylmorpholin-2-yl]methanol and (S)-[4-methoxyphenyl][(2R)-4-benzylmorpholin-2-yl]methanol (118 mg, 0.376 mmol), 2,2'-dimethoxydiphenyldisulphide (210 mg, 0.75 mmol) and tributylphosphine (152 mg, 1.50 mmol) in dry THF (2 ml) was heated at reflux under nitrogen overnight. The reaction mixture was cooled to room temperature and evaporated to an oil. The crude oil was purified by flash chromatography on silica eluting with heptane/ethyl acetate (4/1 then 3/2) to give the product as a colourless oil (95 mg).

iv) (2R)-2-((R)-[4-methoxyphenyl]{[2-methoxyphenyl]thio}methyl)morpholine hydrochloride

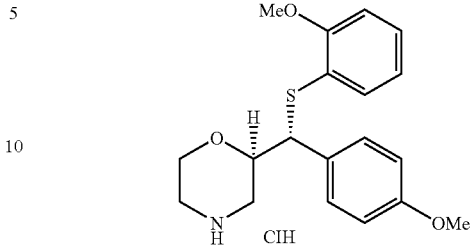

Stirred (2S)-2-((S)-[4-methoxyphenyl]{[2-methoxyphenyl]thio}methyl)-4-benzylmorpholine (2R)-2-((R)-[4-methoxyphenyl]{[2-methoxyphenyl]thio}methyl)-4-benzylmorpholine (618 mg, 1.42 mmol) with solid supported Hunig's base (2.40 g, 8.52 mmol) and α-chloroethyl chloroformate (2.0 g, 14.21 mmol) in dichloromethane (12 ml) at room temperature under nitrogen for 4 h. Filtered and concentrated in vacuo, dissolved oil in methanol and heated at 60° C. for 1.5 h. Cooled to room temperature and purified by SCX column chromatography eluting with ammonia/methanol (ca. 3M) gave a colourless oil. The desired diastereomer was separated on chiralcel-OJ column eluting with heptane/ethanol/dimethylethylamine (20/80/0.2): 8.98 min. The required product was then obtained (60% de) after chiral chromatography on chiralpak-OD column eluting with heptane/isopropanol (70/30): 17.41 min. It was converted into the HCl salt, NMR (DMSO) 9.39 (2H, br. s), 7.3-7.1 (4H, m), 6.94-6.72 (4H, m), 4.6-4.5 (1H, m), 4.12-3.92 (2H, m), 3.85-3.62 (7H, m), 3.46-3.32 (1H, m), 3.20-3.08 (1H, m), 3.04-2.89 (2H, m). LCMS: m/z 346 [M+H]+ @ Rt 4.24 min.

EXAMPLE 2

(2R)-2-((R)-(2-Fluorophenyl){[2-methoxyphenyl]thio}methyl)morpholine hydrochloride i) (2R)-2-[(R)-(2-fluorophenyl)(hydroxy)methyl]-4-benzylmorpholin-3-one, (2S)-2-[(S)-(2-fluorophenyl)(hydroxy)methyl]-4-benzylmorpholin-3-one, (2R)-2-[(S)-(2-fluorophenyl)(hydroxy)methyl]-4-benzylmorpholin-3-one and (2S)-2-[(R)-(2-fluorophenyl)(hydroxy)methyl]-4-benzylmorpholin-3-one

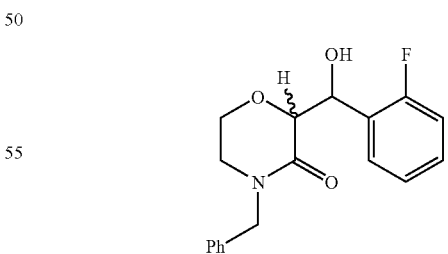

To a stirred solution of (+/−)-4-benzylmorpholin-3-one (10.0 g, 0.052 mol) and 2-fluorobenzaldehyde (7.74 g, 0.062 mol) in dry THF (80 ml) cooled under nitrogen to −78° C. was added dropwise a solution of lithium diisopropylamide in heptane/THF/ethylbenzene (2M, 31.2 ml). After addition, stirred at −78° C. for 0.5 h then allowed to warm to 0° C. before quenching with aqueous saturated ammonium chloride. Concentrated in vacuo and extracted with dichloromethane (2×). The extracts were dried over magnesium sulphate, filtered and evaporated to an oil. Purified on a pad of flash silica eluting with heptane/ethyl acetate (100/0, 80/20, 60/40 and 50/50) to give a 1:1 mixture of the diastereomers as a colourless oil (12.05 g).

ii) (R)-[2-fluorophenyl][(2S)-4-benzylmorpholin-2-yl]methanol and (S)-[2-fluorophenyl][(2R)-4-benzylmorpholin-2-yl]methanol

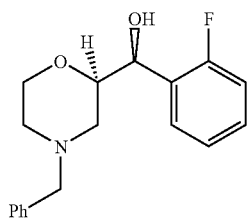

To a stirred solution of (2R)-2-[(R)-(2-fluorophenyl)(hydroxy)methyl]-4-benzylmorpholin-3-one, (2S)-2-[(S)-(2-fluorophenyl)(hydroxy)methyl]4-benzylmorpholin-3-one, (2R)-2-[(S)-(2-fluorophenyl)(hydroxy)methyl]-4-benzylmorpholin-3-one and (2S)-2-[(R)-(2-fluorophenyl)(hydroxy)methyl]-4-benzylmorpholin-3-one (12.0 g, 0.038 mol) in dry THF (80 ml) under nitrogen at room temperature was added a solution of borane in THF (1M, 150 ml). The solution was heated at 60° C. for ca. 4 h then at room temperature overnight. Cooled solution to 0° C. and added dropwise methanol (68 ml) followed by 1NHCl (68 ml). The resulting mixture was heated at 60° C. for 1 h, cooled and concentrated in vacuo. The precipitate was removed by filtration and the filtrate made basic with aqueous sodium carbonate. Extracted with diethyl ether (3×), extracts washed with water and brine, dried over magnesium sulphate, filtered and evaporated to an oil. The crude oil was purified and partially separated by flash chromatography on silica eluting with heptane/ethyl acetate (40/60 to 25/75) to give the product as a colourless oil (0.713 g).

iii) (R)-[2-fluorophenyl][(2S)-4-benzylmorpholin-2-yl]methyl methanesulphonate and (S)-[2-fluorophenyl][(2R)-4-benzylmorpholin-2-yl]methyl methanesulphonate

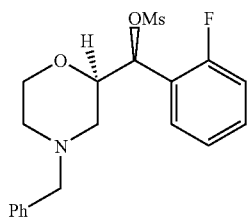

To a stirred solution of (R)-[2-fluorophenyl][(2S)-4-benzylmorpholin-2-yl]methanol and (S)-[2-fluorophenyl][(2R)-4-benzylmorpholin-2-yl]methanol (465 mg, 1.54 mmol) in dry dichloromethane (10 ml) at room temperature under nitrogen was added triethylamine (202 mg, 2.0 mmol) and methanesulphonyl chloride (177 mg, 1.54 mmol). After 15 h, evaporated to an oil and purified by flash chromatography on silica eluting with ethyl acetate/heptane (1/1) to give the product mesylate as a colourless oil (445 mg).

iv) (2R)-2-((R)-[2-fluorophenyl]{[2-methoxyphenyl]thio}methyl)-4-benzylmorpholine and (2S)-2-((S)-[2-fluorophenyl]{[2-methoxyphenyl]thio}methyl)-4-benzylmorpholine

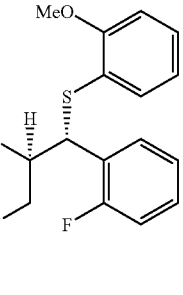

To a stirred suspension of (R)-[2-fluorophenyl][(2S)-4-benzylmorpholin-2-yl]methyl methanesulphonate and (S)-[2-fluorophenyl][(2R)-4-benzylmorpholin-2-yl]methyl methanesulphonate (445 mg, 1.17 mmol) and anhydrous potassium carbonate (0.97 g, 7.02 mmol) in dry degassed DMF (8 ml) under nitrogen at room temperature was added 2-methoxybenzenethiol (0.82 g, 5.87 mmol). After stirring at room temperature for 18 h, diluted with water and extracted with diethyl ether (2×). The extracts were washed with 2NaOH, water and brine, dried over magnesium sulphate, filtered and evaporated to an oil.

After purification by flash column chromatography (eluent:heptane/ethyl acetate 80/20 [v/v]) the title product was obtained as a colourless oil (357 mg); MW 423.55; $C_{25}H_{26}FNO_2S$; $^1H$ NMR (CDCl$_3$): 6.65-7.5 (13H, m), 4.9 (1H, d, 7 Hz), 3.9-4.05 (2H, m), 3.8 (3H, s), 3.6 (1H, dt, 8 Hz and 1 Hz), 3.45 (1H, d, 13.1 Hz), 3.15 (1H, d, 13.1 Hz), 2.60 (2H, t, 8 Hz), 2.05-2.2 (2H, m); FIA: m/z 424 [M+H]$^+$.

v) (2R)-2-((R)-(2-Fluorophenyl){[2-methoxyphenyl]thio}methyl)morpholine hydrochloride

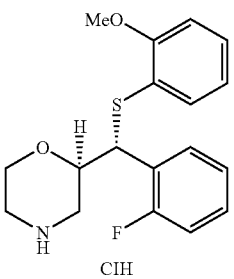

Reaction of the mixture of (2R)-2-((R)-[2-fluorophenyl]{[2-methoxyphenyl]thio}methyl)-4-benzylmorpholine and (2S)-2-((S)-[2-fluorophenyl]{[2-methoxyphenyl]thio}methyl)-4-benzylmorpholine (430 mg, 1.02 mmol) following procedure described in EXAMPLE 1(iv) gave a colourless oil (340 mg, 90% yield) from which the first eluting enantiomer was obtained after chiral chromatography on a Chiralcel-OD column eluant heptane/ethanol/dimethylethylamine (40/60/0.2): Rt 10.41 min. LC purity=98.6 (UV$_{254nm}$); MW 333.43; $C_{18}H_{20}FNOS$.; FIA: m/z 334 [M+H]$^+$. This was converted into the hydrochloride salt. $^1H$ NMR (CDCl$_3$) freebase: 7.2-7.3 (1H, m), 6.85-7.2 (8H, m), 4.85 (1H, d, 8 Hz), 3.95-4.15 (2H, m), 3.85-3.9 (3H, m), 3.7 (1H, dt, 1 Hz and 7 Hz), 2.6-3.0 (4H, m).

EXAMPLE 3

(2R)-2-((R)-[2,5-dichlorophenyl][phenylthio]methyl)morpholine hydrochloride i) (2R)-2-((R)-[2,5-dichlorophenyl][phenylthio]methyl)-4-benzylmorpholine Reacted (2R)-2-[(S)-bromo(phenyl)methyl]-4-benzylmorpholine (150 mg, 0.43 mmol) (see example 8(v) method 2), 2,5-dichlorobenzenethiol (233 mg, 1.30 mmol) and anhydrous potassium carbonate (71 mg, 0.52 mmol) following example 2(iv). The reaction mixture was purified directly by SCX chromatography eluting with ammonia/methanol (ca.3M) to give the product as an oil (174 mg).

ii) (2R)-2-((R)-[2,5-dichlorophenyl][phenylthio]methyl)morpholine hydrochloride

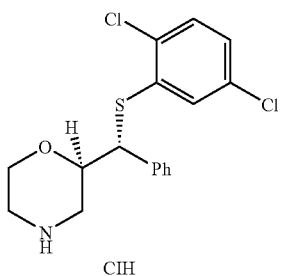

Debenzylation of (2R)-2-((R)-[2,5-dichlorophenyl][phenylthio]methyl)-4-benzylmorpholine (174 mg, 0.39 mmol) with polymer supported Hunig's base (0.20 g, 0.78 mmol) and α-chloroethyl chloroformate (111 mg, 0.78 mmol) following the procedure described in example 1(iv) gave after SCX chromatography the product as an oil (136 mg).

NMR (CDCl$_3$) 7.31-7.14 (7H, m), 7.00 (1H, d), 4.41 (1H, d), 4.06-3.98 (1H, m), 3.90-3.82 (1H, m), 3.7-3.6 (1H, m), 2.94-2.76 (2H, m), 2.65 (2H, d). m/z [M+H] 354/6/8. Crystallised as the HCl salt from ethanol and diethyl ether.

EXAMEPLE 4

(2R)-2-((R)-[2,6-dichlorophenyl][phenylthio]methyl)morpholine hydrochloride i) (2R)-2-((R)-[2,6-dichlorophenyl][phenylthio]methyl)-4-benzylmorpholine Reacted (2R)-2-[(S)-bromo(phenyl)methyl]-4-benzylmorpholine (200 mg, 0.58 mmol) (see example 8(iv) ), 2,6-dichlorobenzenethiol (130 mg, 0.70 mmol) and anhydrous potassium carbonate (97 mg, 0.70 mmol) following example 2(iv). The reaction mixture was purified directly by SCX chromatography eluting with ammonia/methanol (ca. 3M) to give the product as an oil (230 mg).

ii) (2R)-2-((R)-[2,6-dichlorophenyl][phenylthio]methyl)imorpholine hydrochloride

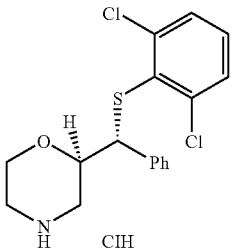

Stirred (2R)-2-((R)-[2,6-dichlorophenyl][phenylthio]methyl)-4-benzylmorpholine (230 mg, 0.52 mmol) with solid supported Hunig's base (270 mg, 1.04 mmol) and α-chloroethyl chloroformate (152 mg, 1.04 mmol) in dichloromethane (4 ml) at room temperature under nitrogen for 3 h. Filtered and concentrated in vacuo, dissolved oil in methanol and stirred at room temperature for 1 h. Evaporated to give a colourless solid. NMR (MeOH) 7.32-7.12 (8H, m), 4.62 (1H, d), 4.31-4.22 (1H, m), 4.16-4.06 (1H, m), 3.91-3.80 (1H, m), 3.2-2.9 (4H, m).

EXAMPLE 5

(2R)-2-((R)-[4-methylphenyl]{[2-methoxyphenyl]thio}methyl)morpholine hydrochloride i) (2R)-2-[(S)-(4-metlylphenyl)(hydroxy)methyl]-4-betizymorpholin-3-one and (2S)-2-[(R)-(4-methylphenyl)(hydroxy)methyl]-4-benzylmorpholin-3-one

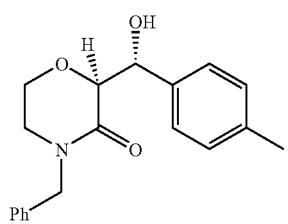

To a stirred solution of (+/−)-4-benzylmorpholin-3-one (4.06 g, 21.3 mmol) in anhydrous THF (25 ml) under nitrogen at −80° C. was added lithium diisopropylamide (2.0M, 19.5 ml) solution in heptane/THF/ethylbenzene dropwise, whilst maintaining the reaction temperature below −65° C. The resulting solution was stirred for a further 30 minutes at −78° C., before being slowly added over approximately 45 minutes to a solution of 4-methylbenzaldehyde (3.07 g, 25.51 mmol) in anhydrous THF (15 ml) under nitrogen at −78° C., whilst again maintaining the reaction temperature below −75° C. The resulting yellow solution was stirred at −78° C. for 0.5 hour, before being allowed to warm to room temperature. The reaction mixture was cautiously quenched by addition of saturated ammonium chloride solution (50 ml) and the THF was evaporated in vacuo from the mixture. The resulting cloudy aqueous solution was extracted with dichloromethane, and the organic extracts were combined, washed with brine, dried over magnesium sulphate, filtered and the dichloromethane evaporated in vacuo to give a thick red oil (9.35 g). After purification by flash column chromatography (eluent: ethyl acetate/hexane 30/70 to 70/30 gradient [v/v]) the colourless oil obtained was triturated with hexane followed by hot cyclohexane to give after successive decanting of supernatant and drying the product as a colourless solid (2.46 g).

ii) (S)-[4-methylphenyl][(2S)-4-benzylmorpholin-2-yl]methanol and (R)-[4-methylphenyl][(2R)-4-benzylmorpholin-2-yl]methanol

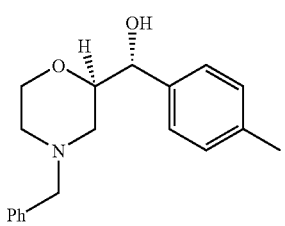

The product was prepared from (2R)-2-[(S)-(4-methylphenyl)(hydroxy)methyl]-4-benzylmorpholin-3-one and (2S)-2-[(R)-(4-methylphenyl)(hydroxy)methyl]-4-benzylmorpholin-3-one (2.50 g, 8.04 mmol) following the procedure described in EXAMPLE 2(ii). The oil was purified by flash chromatography on silica eluting with ethyl acetate/heptane gradient 30/70 to 70/30 to give required product as an oil (1.16 g).

iii) (2R)-2-[(S)-bromo(4-methylphenyl)methyl]-4-benzylmorpholine and (2S)-2-[(R)-bromo(4-methylphenyl)methyl]-4-benzylmorpholine

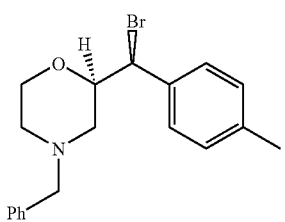

To a stirred solution of (S)-[4-methylphenyl][(2S)-4-benzylmorpholin-2-yl]methanol and (R)-[4-methylphenyl][(2R)-4-benzylmorpholin-2-yl]methanol (1.16 g, 3.91 mmol) and triphenylphosphine (1.54 g, 5.87 mmol) in dry dichloromethane was added dropwise a solution of carbon tetrabromide (1.95 g, 5.87 mmol) in dichloromethane over a period of 10 min. Further triphenylphosphine (0.5 eq) and carbon tetrabromide (0.5 eq) were added after 0.5 h. Quenched reaction mixture after 2 h with saturated aqueous sodium bicarbonate. Extracted with dichloromethane, dried extracts over magnesium sulphate, filtered and evaporated to a red oil. Triturated oil with diethyl ether, filtered and evaporated to a yellow oily solid. The oil was purified by flash chromatography on silica eluting with ethyl acetate/heptane 20/80 to give the product as an oil (0.61 g)

iv) (2R)-2-((R)-[4-methylphenyl]{[2-methoxyphenyl]thio}methyl)-4-benzylmorpholine and (2S)-2-((S)-[4-methylphenyl]{[2-methoxyphenyl]thio}methyl)-4-benzylmorpholine

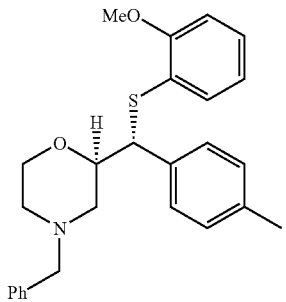

Reacted (2R)-2-[(S)-bromo(4-methylphenyl)methyl]-4-benzylmorpholine and (2S)-2-[(R)-bromo(4-methylphenyl)methyl]-4-benzylmorpholine (340 mg, 0.94 mmol), 2-methoxybenzenethiol (161 mg, 1.13 mmol) and anhydrous potassium carbonate (160 mg, 1.13 mmol) following procedure described in example 2(iv). The crude oil was purified by flash chromatography on silica eluting with ethyl acetate/heptane 20/80 to give the product as an oil (0.21 g).

v) (2R)-2-((R)-(4-methylphenyl){[2-methoxphenyl]thio}methyl)morpholine hydrochloride

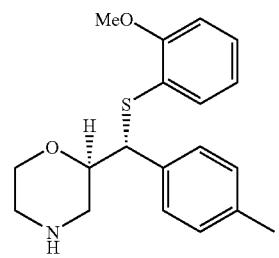

Debenzylation of (2R)-2-((R)-[4-methylphenyl]{[2-methoxyphenyl]thio}methyl)-4-benzylmorpholine and (2S)-2-((S)-[4-methylphenyl]{[2-methoxyphenyl]thio}methyl)-4-benzylmorpholine (210 mg, 0.50 mmol) following procedure described in EXAMPLE 1(iv) but at room temperature gave a colourless oil (180 mg) from which the first eluting enantiomer was obtained after chiral chromatography on a Chiralcel-OD column, elutuant heptane/isopropanol/dimethylethylamine (20/80/0.2) Rt 9.70 min. The oil was dissolved in dichloromethane and HCl/diethyl ether added to give the title compound as the hydrochloride salt (36 mg). NMR (DMSO) 9.20 (2H, br. s), 7.24-7.08 (6H, m), 6.92 (1H, d), 6.89 (1H, t), 4.60 (1H, d), 4.09-3.97 (2H, m), 3.80 (3H, s), 3.78-3.66 (1H, m), 3.20-3.13 (1H, m), 3.04-2.90 (3H, m), 2.24 (3H, s).

EXAMPLE 6

(2R)-2-((R)-[phenyl][2-chlorophenylthio]methyl) morpholine hydrochloride i) (R)-[Phenyl][(2S)-4-benzylmorphoin-2-yl]methyl methanesulphonate and (S)-[Phenyl][(2R)-4-benzylmorpholin-2-yl]methyl methanesulphonate

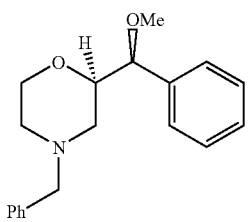

To a stirred solution of (R)-[phenyl][(2S)-4-benzylmorpholin-2-yl]methanol and (S)-[phenyl][(2R)-4-benzylmorpholin-2-yl]methanol (2.0 g, 7.06 mmol) in dry dichloromethane (24 ml) at room temperature under nitrogen was added triethylamine (0.78 g, 7.77 mmol) and methanesulphonyl chloride (0.89 g, 7.77 mmol). After stirring overnight at room temperature, the reaction mixture was diluted with diethyl ether and filtered. The filtrate was evaporated to dryness to give an orange oil (2.5 g).

ii) (2R)-2-((R)-[phenyl]{[2-chlorophenyl]thio}methyl)-4-benzylmorpholine and (2S)-2-((S)-[phenyl]{[2-chlorophenyl]thio}methyl)-4-benzylmorpholine

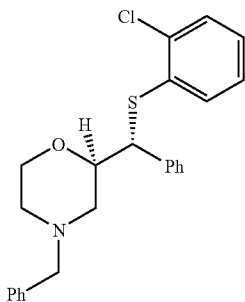

To a stirred suspension of (R)-[phenyl][(2S)-4-benzylmorpholin-2-yl]methyl methanesulphonate and (S)-[phenyl][(2R)-4-benzylmorpholin-2-yl]methyl methanesulphonate (790 mg, 2.19 mmol) and anhydrous potassium carbonate (1.50 g, 10.95 mmol) in dry degassed DMF (3 ml) under nitrogen at room temperature was added 2-chlorobenzenethiol (1.58 g, 10.95 mmol). After stirring at room temperature for 18 h, diluted with water and extracted with dichloromethane (2×). The extracts were washed with 2N NaOH, water and brine, dried over magnesium sulphate, filtered and evaporated to an oil. After purification by flash column chromatography (eluent: heptane/ethyl acetate 100/0 to 70/30 [v/v]) the product was obtained as a colourless oil (0.26 g)

iii) (2R)-2-((R)-[phenyl][2-chlorophenylthio]methyl)morpholine hydrochloride

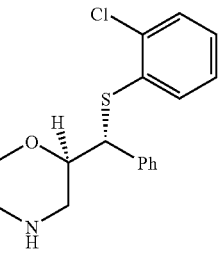

Debenzylation of (2R)-2-((R)-[phenyl]{[2-chlorophenyl]thio}methyl)-4-benzylmorpholine and (2S)-2-((S)-[phenyl]{[2-chlorophenyl]thio}methyl)-4-benzylmorpholine (250 mg, 0.61 mmol) following procedure described in EXAMPLE 1(iv) but at room temperature gave a colourless oil (190 mg) from which the first eluting enantiomer was obtained after chiral chromatography on a ChiralPak-AD column eluant heptane/ethanoldimethylethylamine (85/15/0.2) Rt 7.55 min. NMR (DMSO) 9.34 (2H, br. s), 7.31-7.00 (9H, m), 4.68 (1H, d), 4.09-3.90 (1H, m), 3.98-3.87 (1H, m), 3.69-3.58 (1H, m), 3.10-3.01 (1H, m), 2.90-2.79 (3H, m). Converted to the title product hydrochloride salt.

EXAMPLE 7

(2R)-2-((R)-[phenyl][2-methylphenylthio]methyl) morpholine hydrochloride i) (2R)-2-((R)-[phenyl]{[2-methylphenyl]thio}methyl)-4-benzylmorpholine and (2S)-2-((S)-[phenyl]{[2-methylphenyl]thio}methyl)-4-benzylmorpholine

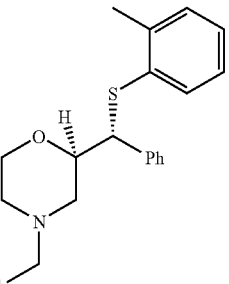

The product was prepared as an oil (0.22 g) from (R)-[phenyl][(2S)-4-benzylmorpholin-2-yl]methyl methanesulphonate and (S)-[phenyl][(2R)-4-benzylmorpholin-2-yl] methyl methanesulphonate (0.49 g, 1.46 mmol), 2-methylbenzenethiol (0.22 g, 1.75 mmol) and potassium carbonate (0.24 g, 1.75 mmol) following the procedure described in EXAMPLE 6(ii)

ii) (2R)-2-((R)-[phenyl][2-methlylphenylthio]methyl)morpholine hydrochloride

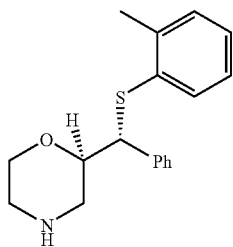

Debenzylation of (2R)-2-((R)-[phenyl]{[2-methylphenyl]thio}methyl)-4-benzylmorpholine and (2S)-2-((S)-[phenyl]{[2-methylphenyl]thio}methyl)-4-benzylmorpholine (210 mg, 0.54 mmol) following procedure described in EXAMPLE 1(iv) but at room temperature gave a colourless oil (180 mg) from which the first eluting enantiomer was obtained after chiral chromatography on a ChiralPak-OJ column eluant heptane/ethanol/dimethylethylamine (40/60/0.2) Rt 8.86 min. This was converted to the title product hydrochloride salt and crystallised from isopropanol/methanol. NMR (CDCl$_3$) 10.06 (2H, br. s), 7.20-6.93 (9H, m), 4.35-4.27 (1H, m), 4.10-3.93 (3H, m), 3.22-3.11 (2H, m), 3.03-2.86 (2H, m), 2.28 (3H, s).

EXAMPLE 8

(2R)-2-((R)-[phenyl][2-trifluoromethylphenylthio]methyl)morpholine hydrochloride

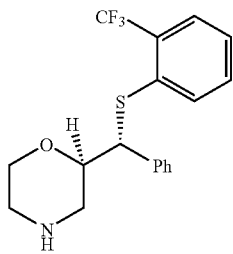

Method 1

(i) 4-Benzylmorpholin-3-one

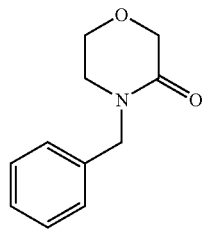

A solution of N-benzyl-N-(2-hydroxyethyl)chloroacetamide (1.0 eq., 627.7 g, 2.759 mol) in tert-butanol (0.9 L) was stirred under nitrogen while warming to 25-30° C. A 1.0 M solution of potassium tert-butoxide in tert-butanol (1.05 eq., 2.897 L, 2.897 mol) was added over 2 hours, maintaining the reaction temperature between 30 and 32° C. The reaction mixture was stirred at 27-28° C. for 90 minutes. When TLC showed the reaction to be complete, ice-cold water (6 L) was added and the resultant cloudy solution extracted with EtOAc (1×3 L, 2×1.5 L). The combined organic layers were washed with brine (2×3 L), dried over MgSO4 and evaporated in vacuo to give a light brown oil (441 g, 84% yield), which was used in the next stage without further purification; MW 191.23; C11H13NO2; Rf 0.52 (80% EtOAc, 20% hexane); 1H NMR (CDCl3): 7.40-7.29 (5H, m), 4.67 (2H, s), 4.28 (2H, s), 3.87 (2H, t, 5.4 Hz), 3.31 (2H, t, 5.4 Hz); LCMS: m/z 192 [M+H]+@ Rt 1.00 min (single major peak).

(ii) (2R)-4-benzyl-2-[(S)-hydroxy(phenyl)methyl]morpholin-3-one, (2S)-4-benzyl-2-[(R)-hydroxy(phenyl)methyl]morpholin-3-one and (2R)-4-benzyl-2-[(R)-hydroxy(phenyl)methyl]morpholin-3-one, (2S)-4-benzyl-2-[(S)-hydroxy(phenyl)methyl]morpholin-3-one

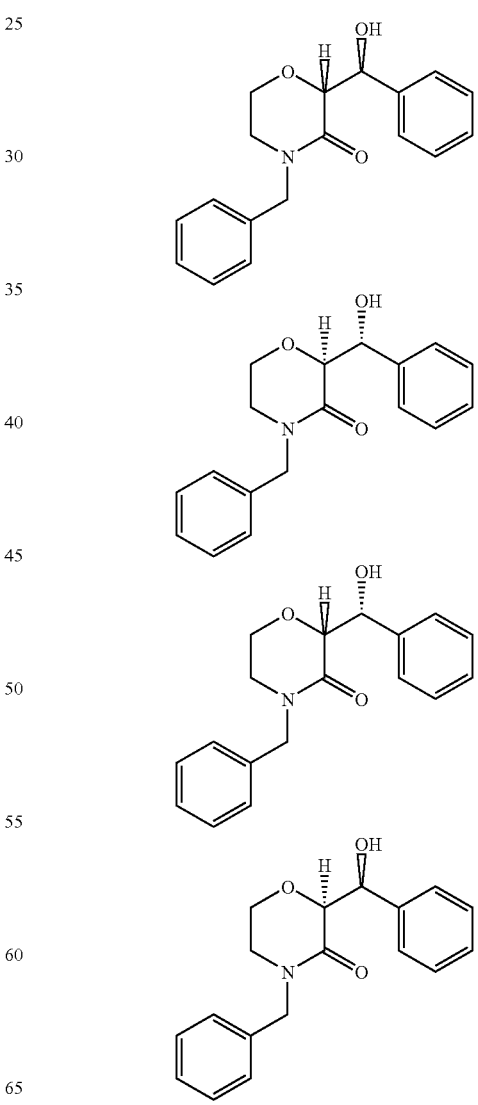

To a stirred solution of 4-benzylmorpholin-3-one (5.02 g, 26 mmol) in anhydrous THF (25 ml) under nitrogen at −78° C. was added a 2 M. solution of LDA in heptane/THF/ethylbenzene (1.5 eq., 39 mmol, 19.5 ml) over approximately 20 minutes, whilst maintaining the reaction temperature below −75° C. The resulting brown solution was stirred for a further 30 minutes at −78° C., before being slowly added over approximately 30 minutes to a solution of benzaldehyde (1.2 eq., 3.34 g, 31 mmol) in anhydrous THF (15 ml) under nitrogen at −78° C., whilst again maintaining the reaction temperature below −75° C. The resulting yellow solution was stirred at −78° C. for 1 hour, before being allowed to warm to room temperature slowly over 1 hour. The reaction mixture was cautiously quenched by addition of saturated ammonium chloride solution (50 ml) and the THF was evaporated in vacuo from the mixture. The resulting cloudy aqueous solution was extracted with DCM (3×50 ml), and the organic extracts were combined, washed with brine (50 ml), dried over Na$_2$SO$_4$ and the DCM evaporated in vacuo to give a thick brown oil (9.2 g), which partially crystallised on standing. The mixture of diastereoisomeric alcohols was purified and separated by flash column chromatography using gradient elution (from 10% EtOAc, 90% DCM to 20% EtOAc, 80% DCM), which gave (2R)-4-benzyl-2-[(S)-hydroxy(phenyl)methyl]morpholin-3-one and (2S)-4-benzyl-2-[(R)-hydroxy(phenyl)methyl]morpholin-3-one as light red crystals (2.461 g, 31% yield); MW 297.36; C18H19NO3; Rf 0.40 (50% EtOAc, 50% hexane); 1H NMR (CDCl3): 7.41-7.36 (2H, m), 7.31-7.16 (6H, m), 6.91-6.86 (2H, m), 5.14 (1H, d, J 3.5 Hz), 4.71 (1H, d, 14.5 Hz), 4.48 (1H, d, J 3.5 Hz), 4.25 (1H, d, 14.5 Hz), 4.20 (1H, br. s), 3.89 (1H, ddd, 11.7 Hz, 2.5 Hz, 2.0 Hz), 3.67 (1H, dt, 11.2 Hz, 3.4 Hz), 3.16 (1H, dt, 12.0 Hz, 4.0 Hz), 2.86 (1H, br. d, 12.0 Hz); LCMS: m/z 298 [M+H]+ @ Rt 1.24 min (single major peak). This reaction was performed on scales from 200 mg to 5 g (yield range 20 to 40%). (2R)-4-benzyl-2-[(R)-hydroxy(phenyl)methyl]morpholin-3-one and (2S)-4-benzyl-2-[(S)-hydroxy(phenyl)methyl]morpholin-3-one diastereoisomer was isolated as a brown solid (1.42 g) contaminated with N-benzylmorpholin-3-one. Trituration with EtOAc afforded the pure compound as a white solid (0.484 g, 6% yield); MW 297.36; C18H19NO3; Rf 0.23 (50% EtOAc, 50% hexane); 1H NMR (CDCl3): 7.61-7.55 (2H, m), 7.50-7.36 (6H, m), 7.31-7.25 (2H, m), 5.21 (1H, d, 2.3 Hz), 5.09 (1H, d, J 7.7 Hz, 2.3 Hz), 4.73 (2H, s, s Hz), 4.37 (1H, d, J 7.7 Hz), 4.01(1H, ddd, 12.0 Hz, 2.6 Hz, 1.9 Hz), 3.77 (1H, dt, 11.0 Hz, 3.5 Hz), 3.50 (1H, dt, 12.0 Hz, 4.0 Hz), 3.16 (1H, br. d, 12.0 Hz); LCMS: m/z 298 [M+H]+ @ Rt 1.24 min (single major peak).

(iii) (S)-[(2S)-4-benzylmorpholinyl](phenyl)methanol and (R)-[(2R)-4-benizylmorpholinyl](phenyl)methanol

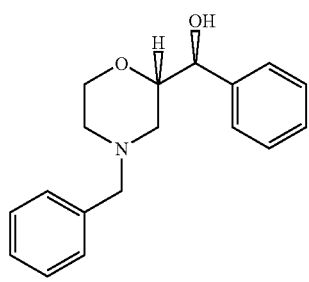

-continued

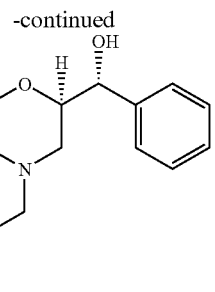

To a solution of (2R)-4-benzyl-2-[(S)-hydroxy(phenyl)methyl]morpholin-3-one and (2S)-4-benzyl-2-[(R)-hydroxy(phenyl)methyl]morpholin-3-one (326 mg, 1.1 mmol) in anhydrous THF (5 ml) under nitrogen at room temperature was slowly added a 1 M solution of borane in THF (4 eq., 4.4 ml, 4.4 mmol). The solution was stirred at 60° C. for 2 hours. After cooling down to room temperature, dry methanol (2 ml) was slowly added to quench excess borane reagent. 1 M. Aqueous hydrochloric acid solution (2 ml) was added and the reaction mixture was heated to 60° C. for 1 hour. The organic solvents were evaporated in vacuo and the concentrated solution was poured onto 1 M aqueous potassium carbonate solution (10 ml) and extracted with diethyl ether (2×20 ml). The combined organic layers were washed with brine (20 ml), water (20 ml), dried over MgSO4 and concentrated in vacuo. The resultant oil was purified by flash column chromatography (90% hexane, 9% EtOAc, 1% NEt3) to give a viscous oil (189 mg, 60% yield); MW 283.37; C18H21NO2; Rf 0.42 (90% EtOAc, 10% hexane); 1H NMR (CDCl3): 7.45-7.32 (10H, m), 4.67 (1H, d, 7.3 Hz), 4.03 (1H, dt, 11.4 Hz, 2.7 Hz), 3.86-3.73 (2H, m), 3.64 (1H, d, 13.2 Hz), 3.39 (1H, d, 13.2 Hz), 3.30 (1H, br. s), 2.68 (1H, d, 12.7 Hz), 2.56 (1H, d, 10.9 Hz), 2.28-2.15 (2H, m); LCMS: m/z 284 [M+H]+ @ Rt 0.95 min (single major peak).

This reaction was performed on scales from 50 mg to 1.5 g (yield range=50 to 84%).

(iv) (R)-[(2S)-4-benzylmorpholinyl](phenyl)methanol and (S)-[(2R)-4-benzylmorpholinyl](phenyl)methanol

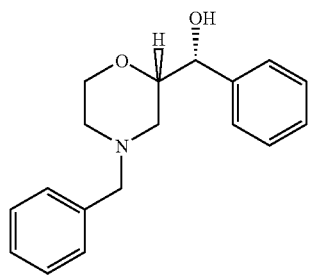

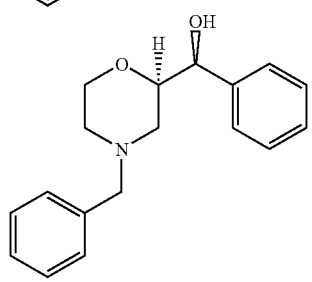

Using the procedure described in Example 8(iii) starting from (2R)-4-benzyl-2-[(R)-hydroxy(phenyl)methyl]-morpholin-3-one and (2S)-4-benzyl-2-[(S)-hydroxy(phenyl)methyl]-morpholin-3-one (135 mg, 0.51 mmol) the reaction and subsequent purification yielded a viscous oil (98 mg, 68% yield); MW 283.37; $C_{18}H_{21}NO_2$; Rf 0.52 (100% EtOAc); 1H NMR (CDCl3): 7.28-7.17 (10H, m), 4.80 (1H, d, 4.0 Hz), 3.88 (1H, dt, 11.4 Hz, 3.0 Hz), 3.72 (1H, m), 3.68-3.61 (1H, m), 3.50 (1H, d, 13 Hz), 3.25 (1H, d, 13 Hz), 2.52 (2H, br. t, 12.0 Hz), 2.17 (1H, t, 11 Hz), 2.08 (1H, td, 11 Hz, 3.0 Hz), OH not observed; LCMS: m/z 284 [M+H]+ @ Rt 0.98 min (single major peak). This reaction was performed on scales from 100 to 400 mg (yield range=60 to 93%).

(v) (2R)-4-benzyl-2-[(S)-bromo(phenyl)methyl]morpholine and (2S)-4-benzyl-2-[(R)-bromo(phenyl)methyl]morpholine

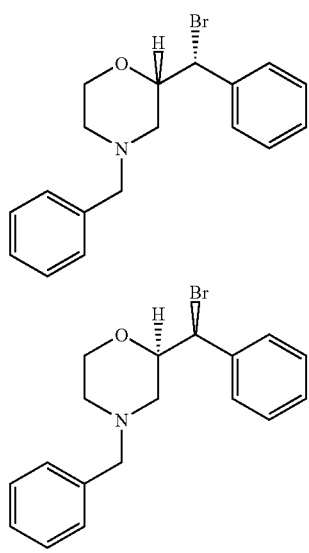

To a solution of (S)-[(2S)-4-benzylmorpholinyl](phenyl)methanol and (R)-[(2R)-4-benzylmorpholinyl](phenyl)methanol (10.27 g, 36.29 mmol) in anhydrous dichloromethane (150 ml) under nitrogen at room temperature was added freshly recrystallised triphenylphosphine (1.4 eq., 13.310 g, 50.80 mmol) followed by carbon tetrabromide (1.4 eq., 16.849 g, 50.80 mmol) as a solution in anhydrous dichloromethane (50 ml). After 15 minutes the reaction mixture was diluted with dichloromethane (100 ml) and washed with saturated aqueous sodium hydrogencarbonate solution (150 ml), brine (150 ml), dried over MgSO4 and concentrated in vacuo to give an orange oil (42.0 g). To the orange oil was added diethyl ether (200 ml) and the resulting suspension was sonicated for 30 minutes. The solvent was decanted and the process repeated with a further portion of diethyl ether (200 ml). The combined ethereal extracts were concentrated in vacuo to yield an orange solid (22.0 g) which was purified by flash column chromatography (10% EtOAc: 89.5% Hexane, 0.5% Triethylamine) to give a white solid (7.20 g, 58% yield). Alternative Work-up: The reaction mixture was poured onto a silica (160 g) filtration pad which was washed using suction with dichloromethane (14×250 ml). Stripping this filtrate in vacuo gave crude product (16.0 g, 131% uncorrected). This was purified by flash column chromatography (5% EtOAc: 94.5% Hexane: 0.5% Triethylamine to 10% EtOAc: 89.5% Hexane: 0.5% Triethylamine) to give a white solid (6.05 g, 50% yield); MW 346.27; C18H20BrNO; Rf 0.76 (70% EtOAc, 30% hexane); 1H NMR (CDCl3): 7.39-7.14 (10H, m), 4.83 (1H, d, 7.4 Hz), 4.01 (1H, br. t, 8.3 Hz), 3.73 (1H, br. d, 11.1 Hz), 3.60-3.48 (2H, m), 3.39 (1H, d, 12 Hz), 3.20 (1H, d, 11.4 Hz), 2.50 (1H, d, 10.4 Hz), 2.07 (2H, t, 10.9 Hz); LCMS: m/z 348/346 [M+H]+ @ Rt 1.20 min (single major peak). This reaction was performed on scales from 100 to 400 mg (yield range=60 to 93%).

A sample of racemic (2R)-4-benzyl-2-[(S)-bromo(phenyl)methyl]morpholine and (2S)-4-benzyl-2-[(R)-bromo(phenyl)methyl]morpholine (6.02 g) was separated by preparative chiral chromatography (Chiralcel-AD 1 kg column, ethanol:dimethylethylamine 100: 0.3) to give the first eluting enantiomer Rt 23.4 min as an off-white solid (2.89 g) of (2R)-4-benzyl-2-[(S)-bromo(phenyl)methyl]morpholine and the second eluting enantiomer Rt 28.9 min as an off-white solid (2.89 g) of (2S)-4-benzyl-2-[(R)-bromo(phenyl)methyl]morpholine (2.21 g)

vi) (2R)-2-((R)-[phenyl]{[2-trifluoromethylphenyl]thio}methyl)-4-benzylmorpholine and (2S)-2-((S)-[phenyl]{[2-trifluoromethylphenyl]thio}metlyl)-4-benzylmorpholine

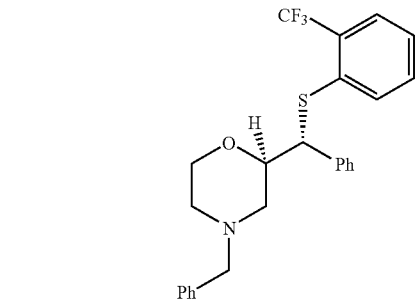

To a stirred solution of 2-trifluoromethylthiophenol (2.469 g, 13.86 mmol) and (2R)-2[(S)-bromo(4-methylphenyl)methyl)-4-benzylmorpholine and (2S)-2[(R)-bromo(4-methylphenyl)methyl)-4-benzylmorpholine (4.0 g, 11.55 mmol) in anhydrous DMF (60 ml) at room temperature under nitrogen was added cesium carbonate (4.14 g, 12.71 g). The reaction mixture was heated at 95° C. for 1 h. The reaction mixture was cooled to room temperature, diluted with ethyl acetate, then washed sequentially with water, brine, dried over magnesium sulphate, filtered and evaporated to a brown oil. The oil was purified by flash column chromatography (eluent: hexane/ethyl acetate gradient 100 to 90/10 [v/v]) to give a yellow oil (4.83 g, 94% yield); MW 444; $C_{25}H_{24}F_3NOS$; $^1H$ NMR (CDCl$_3$): 7.60 (1H, dd, 7.2 Hz, 1.4 Hz), 7.17-7.39 (13H, m), 4.50 (1H, d, 7.2 Hz), 3.97-4.12 (2H, m), 3.73 (1H, dt, 9.7 Hz, 2.3 Hz), 3.59 (1H, d, 12.6 Hz), 3.37 (1H, d, 12.6 Hz), 2.57-2.68 (2H, m); 2.18-2.38 (2H, m); LCMS (2.5 minutes method): m/z 445 [M+H]+ @ Rt 1.50 min.

vii) (2R)-2-((R)-[phenyl][2-trifluoromethylphenylthio]methyl)morpholine hydrochloride

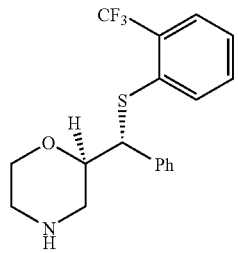

The title compound was obtained from (2R)-2-((R)-[phenyl]{[2-trifluoromethylphenyl]thio}methyl)-4-benzylmorpholine and (2S)-2-((S)-[phenyl]{[2-trifluoromethylphenyl]thio}methyl)-4-benzylmorpholine (5.25 g, 11.84 mmol), solid supported Hunig's base (Argonaut, 3.56 mmol/g, 6.64 g, 23.67 mmol, 2 eq.) and α-chloroethyl chloroformate (3.83 ml, 35.51 mmol, 3 eq.) in anhydrous dichloromethane (75 ml) at 40° C. following the method described in example 1(iv). After evaporation of the methanol solution a light brown solid (5.60 g) was obtained which was recrystallised from iso-propanol to give the hydrochloride salt as fine white needles. The hydrochloride salt was suspended in ethyl acetate and washed with an aqueous solution of sodium hydroxide (50 ml of a 1M solution). The organic layer was washed with brine, dried over $MgSO_4$ and concentrated in vacuo to yield the free amine as a colourless oil (3.10 g, 74% yield); MW 353.41; $C_{18}H_{18}F_3NOS$; $^1$H NMR ($CDCl_3$): 7.46 (1H, d, 7.7 Hz), 7.24 (1H, d, 7.3 Hz), 7.05-7.2 (7H, m), 4.28 (1H, d, 7.7 Hz), 3.92 (1H, d, 11.4 Hz), 3.80 (1H, q, 7.0 Hz), 3.58 (1H, dt, 1.82 Hz, 11.4 Hz), 2.69-2.87 (2H, m), 2.59 (2H, d, 6.0 Hz), 2.13-1.90 (1H, br s); LCMS (10 minutes method): m/z 354 [M+H]+ @ Rt 5.26 min.

A sample of the racemic free base (1.384 g) was separated by preparative chiral chromatography (Chiralpak-OJ, heptane: isopropanol: dimethylethylamine 70: 30: 0.2) to give the first eluting enantiomer Rt 9.5 min (0.57 g) as an oil. Redissolved in diethyl ether (20 ml) and treated with ethereal hydrogen chloride (2M 0.8 ml) to give a white solid (566 mg, mp 240-1° C.) of the title product (2R)-2-((R)-[phenyl][2-trifluoromethylphenylthio]methyl)morpholine hydrochloride.

The second eluting enantiomer Rt 15.8 min was obtained as an oil (0.55 g) and similarly converted to the hydrochloride salt (2S)-2-((S)-[phenyl][2-trifluoromethylphenylthio]methyl)morpholine hydrochloride (556 mg mp 244-5° C.). A sample (20 mg) was crystallised from isopropanol (2 ml) allowing the solvent to evaporate slowly over several weeks. The crystals were analysed by xray crystallography to confirm the absolute stereochemistry as (S,S) for the second eluting enantiomer, data is listed in tables 1-6 herein.

Method 2

(i) 4-benzyl-morpholine-2-carbonitrile

A one-liter reactor with mechanical stirring, cooled by ice bath, was charged with N-benzylethanolamine (172.2 g, 1.14 mol). 2-Chloroacrylonitrile (100 g, 1.14 mol) was added dropwise over a period of 2 minutes. The temperature was kept between 23° C. and 29° C. using an ice bath, progressively replaced by a water bath at 15° C. After stirring at room temperature over night the mixture was dissolved in THF and transferred into a 2l reactor cooled to −5° C. by an ice/NaCl bath. The total volume of THF equalled 1.351. Potassium tert-butoxide (148 g, 1.1 eq.) was added in portions over 1 hour, while maintaining the temperature at 0±2° C. After 1 hour stirring at 0° C. the mixture was quenched by saturated $NaHCO_3$ (500 ml). The aqueous layer was extracted with diethyl ether. The organic layers were dried over $MgSO_4$ and evaporated to dryness. After percolation of the 250 g dry residue on 1 kg $SiO_2$ (eluent: ethyl acetate/n-heptane gradient 5/95 to 80/100 [v/v]) 4-benzyl-morpholine-2-carbonitrile was obtained as a clear oil (149.8 g, 65%).

(ii) (2S)-(4-Benzyl-morpholin-2-yl)-phenyl-methanone and (2R)-(4-Benzyl-morpholin-2-yl)-phenyl-methanone

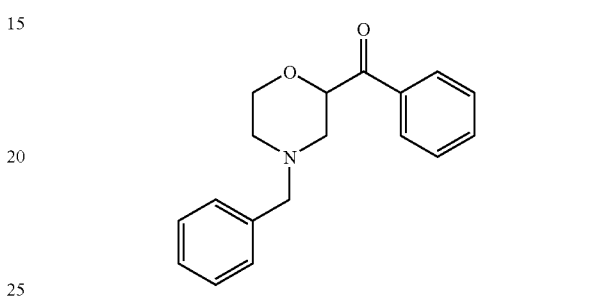

A 3l double jacket reactor was charged with 4-benzyl-morpholine-2-carbonitrile (135.05 g; 1 eq) and dry diethyl ether (1.4l). Alternatively, toluene may be used in place of diethyl ether. When Tj=0° C. and Tm=1° C. (Tj=temperature of the jacket, Tm=temperature of the mass), phenyl magnesium chloride (2M sol. in THF, 360 ml, 1.08 equiv) was added dropwise over 1 hour. Tm rose to 4° C. and came back to 2° C. at the end of the addition. Tm was progressively raised to 17.5° C. within 45 minutes and the mixture stirred at this temperature for another 45 minutes. The reactor was cooled down to Tm=2° C. and Tj=0° C. (75 minutes) and hydrochloric acid (700 ml of 5N solution) was added in two portions. Tm rose to 33° C. After some minutes, the hydrochloride salt of the ketone crystallised. When Tm=Tj=room temperature, the triphasic suspension was filtered. The organic layer of the mother liquors, which contains impurities, was eliminated. The filtration cake was then washed with methylene chloride (700 ml). This liquor was charged in the reactor with the acid aqueous layer. Treatment of the hydrochloride salt: After drying under vacuum, 164.4 g of the hydrochloride contaminated with $MgCl_2$ were suspended in a biphasic mixture of water/methylenechloride (500 ml/800 ml). The suspension was basified with aqueous sodium hydroxide (75 ml of a 30% solution) under ice bath cooling. $Mg(OH)_2$ precipitated and the aqueous layer was extracted with methylene chloride. The organic layers are filtered on a bed of Celite 512 after adding some Celite to the layers themselves. The filtered organic phase was dried over $MgSO_4$ and evaporated to dryness. The ketone crystallizes readily on standing (132.4 g; 70%). Treatment of the mother liquors: The combined organic phases were washed with aqueous sodium hydroxide (750 ml of a 2N solution). Celite 512 (160 g) was added to the suspension which was then filtrated through bed of Celite. The aqueous layer was separated and extracted with methylene chloride. The combined organic phases were dried over $MgSO_4$ and evaporated to dryness to provide 35.8 g of product enriched with unreacted nitrile. This fraction could be further purified by percolation on $SiO_2$. (2S)-(4-benzyl-morpholin-2-yl)-phenyl-methanone and (2R)-(4-benzyl-morpholin-2-yl)-phenyl-methanone were separated using preparative chiral chromatography. Alternatively, the two enantiomers may be separated by fractional crystallization from acetonitrile using from 0.55 to 1 equivalent of dibenzoyltartaric acid to generate diastereoisomeric salts of the title compound. The crystals may be collected by filtration and neutralized with 30% NaOH to afford the optically enriched title compound.

The title compound may also be prepared using the following one-pot synthesis. A 1600 L GL reactor under $N_2$ was successively loaded with 2-chloroacrylonitrile (33.2 kg, 379 moles) and toluene (114 L) at 21° C. Then, N-benzylethanolamine (57 kg, 377 moles) was added and the reaction mixture was post-agitated at room temperature for about 17 h. Then, the mixture was diluted with toluene (336 L), cooled down to −12.4° C. and potassium t-butoxide (42.3 kg, 377 moles) was added in portions (10) maintaining −13.7° C.≦Tmass≦−2.8° C. The mixture was post-agitated at about 0° C. for 2.5 h, quenched by adding ultra pure water (142.5 L) maintaining 2.1° C.≦Tmass≦8.7° C. The aqueous layer (176 kg) was separated after 35 minutes of post-stirring allowing the mixture to reach 15° C. and the toluene layer was washed with ultra pure water (142.5 L) and the aqueous layer (162 kg) was separated. The organic layer was then concentrated under reduced pressure (150 mbars) maintaining Tmass≦60° C. in order to distill 162 kg of toluene. The filtrates were then diluted with toluene (114 L) and treated with $SiO_2$ (Merck silica gel 60, 0.063-0.1 mm, 74.1 kg) under agitation at room temperature for 1.25 h. $SiO_2$ was filtered and rinsed with toluene (2×114 L). Then, the filtrates were concentrated under reduced pressure (150 mbars) maintaining Tmass≦60° C. in order to distill 351.8 kg of toluene (KF: 0.01% w/w $H_2O$).

The solution of 4-Benzyl-morpholine-2-carbonitrile (169.2 kg) was diluted with toluene (157 L) and was cooled to 0° C. and phenylmagnesiumchloride (25 wt. % solution in THF, 213 kg, 389 moles, 1.36 molar equiv.) was slowly added (over 3.5 h) to the reaction mixture, maintaining the temperature at −3° C.≦Tmass≦7° C. The reaction mixture was post-stirred for 2 hours at Tmass≈0° C. Then, the quench was performed by adding acetic acid (8.55 L, Tmass=5→17.2° C.), post stirring 10 minutes and cooling to 5° C. before adding an acetic acid/water mixture (229 L, 33/67 v/v). During the quench, addition was performed at such a rate that Tmass did not exceed 20° C. (typical Tmass=4.6° C. to 10.4° C.). The mixture was post-agitated overnight at RT and the aqueous layer (285.8 kg) was extracted.

The toluene layer was cooled to 0° C. and a 5 N NaOH aqueous solution (420.1 kg) was slowly added maintaining the temperature at −2.4° C.≦Tmass≦11° C. The reaction mixture was post-stirred for 1 h and the aqueous layer (494.8 kg) was extracted. The toluene layer was concentrated under reduced pressure (50 mbars) maintaining Tmass≦60° C. in order to distill 356.2 kg of toluene and isopropanol (180.4 kg) was added. The toluene was stripped off under reduced pressure (100 mbars) maintaining Tmass≦60° C. in order to distill 186.4 kg of toluene and isopropanol (135 kg) was added again to the mixture. A last distillation of toluene was performed under reduced pressure (50 mbars) maintaining Tmass≦60° C. in order to distill 131 kg of toluene and isopropanol (49.4 kg) was finally added to the mixture and the solution was stirred at RT until crystallization (17 minutes).

Ultra pure water was added (125.4 L) and the mixture was stirred overnight at RT and cooled down to about 0° C. for 1 hour. The precipitate was filtered and rinsed with a cooled water/isopropanol 50/50 v/v solution (76.6 kg). The wet precipitate was dried under vacuum at Tjack=35° C. for 96 hours to obtain the title compound as an off-white powder with 59% overall yield. The title compound may be resolved by the fractional crystallisation process described above.

(iii) (R)-phenyl[(2R)-4-(phenylmethyl)morpholin-2-yl]methanol

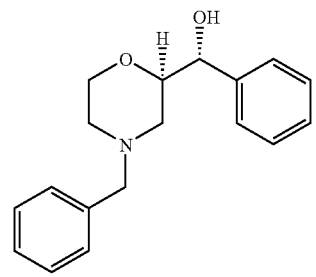

To a stirred solution of (+)-DIP chloride (49.6 g, 155 mmol) in dry TBF (150 ml) under nitrogen was added (2R)-(4-benzyl-morpholin-2-yl)-phenyl-methanone (16.54 g, 58.89 mmol) in one portion. The reaction mixture was stirred at room temperature for 18 hours. The mixture was evaporated in vacuo and the crude oil taken up in methanol and absorbed onto 250 g SCX-2 ion exchange resin. After elution of borane residues with methanol the product was eluted with 2M ammonia in methanol. Removal of solvent in vacuo yielded the product as yellow oil. (11.23 g, 67%); MW 283.37; $C_{18}H_{21}NO_2$; $^1H$ NMR ($CDCl_3$): 7.32-7.45 (10H, m), 4.67 (1H, d, 7.3 Hz), 4.03 (1H, dt, 11.4 Hz, 2.7 H), 3.86-3.73 (2H, m), 3.64 (1H, d, 13.2 Hz), 3.39 (1H, d, 13.2 Hz), 3.30 (1H, br. s), 2.68 (1H, d, 12.7 Hz), 2.56 (1H, d, 10.9 Hz), 2.28-2.15 (2H, m); LCMS: m/z 284 [M+H]+ @ Rt 0.95 min.

(v) (2R)-2-[(S)-bromo(phenyl)methyl]-4-(phenylmethyl)morpholine

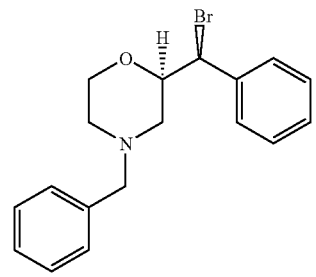

To a solution of (R)-phenyl[(2R)-4-(phenylmethyl)morpholin-2-yl]methanol (11.2 g, 39.58 mmol) in anhydrous chloroform (400 ml) under nitrogen was added $PPh_3Br_2$ (33.41 g, 79.15 mmol). The reaction mixture was heated at 60° C. overnight. The mixture was allowed to cool to room temperature then washed with saturated aqueous sodium carbonate solution, dried over $MgSO_4$ and concentrated in vacuo. The resulting residue was purified by flash chromatography on silica (eluent: ethyl acetate:isohexane 1:4) to give a pale yellow oil. Trituration with isohexane gave (2R)-2-[(S)-bromo(phenyl)methyl]-4-(phenylmethyl)morpholine as a colourless solid (8.54 g, 62%); MW 346.27; $C_{18}H_{20}BrNO$; $^1H$ NMR ($CDCl_3$): 7.14-7.39 (10H, m), 4.83 (1H, d, 7.4 Hz), 4.01 (1H, br. t, 8.3 Hz), 3.73 (1H, br. d, 11.1 Hz), 3.60-3.48 (2H, m), 3.39 (1H, d, 12 Hz), 3.20 (1H, d, 11.4 Hz), 2.50 (1H, d, 10.4 Hz), 2.07 (2H, t, 10.9 Hz); LCMS: (6 min method) m/z 346 [M]+ @ Rt 2.51 min.

(vi) (2R)-2-[(S)-bromo(phenyl)methyl]-4-(phenylmethyl)morpholine can then be Converted to the Title Product (2R)-2-((R)-[phenyl][2-trifluoromethylphenylthio]methyl)morpholine hydrochloride using the above Procedure in example 8 Method 1 (v) and (vi).

EXAMPLE 9

(2R)-2-[(R)-[(2-ethylphenyl)thio](phenyl)methyl]morpholine i) (2S)-2-[(S)-[(2-ethylphenyl)thio](phenyl)methyl]-4-(phenylmethyl)morpholine and (2R)-2-[(R)-[(2-etlylphenyl)thio](phenyl)methyl]-4-(phenylmethyl)morpholine

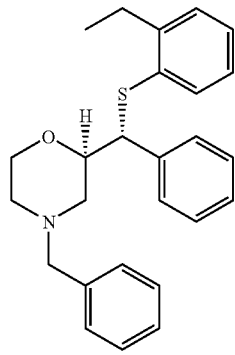

Compound (2S)-2-[(S)-[(2-ethylphenyl)thio](phenyl)methyl]-4-(phenylmethyl)morpholine and (2R)-2-[(R)-[(2-ethylphenyl)thio](phenyl)methyl]-4-(phenylmethyl)morpholine was obtained from 2-ethyl-thiophenol (160 mg, 1.16 mmol) and (2R)-4-benzyl-2-[(S)-bromo(phenyl)methyl]morpholine and (2S)-4-benzyl-2-[(R)-bromo(phenyl)methyl]morpholine (200 mg, 0.58 mmol) following a modification of the method described in example 8(vi) in which the reaction mixture was heated to 95° C. for 2 hours. After purification by flash column chromatography (eluent: ethyl acetate/hexane 9/1 [v/v]) the product was obtained as a white solid (152 mg, 65% yield); MW 403.59; $C_{26}H_{29}NOS$; $^1H$ NMR (CDCl$_3$): 6.96-7.40 (14H, m), 4.22 (1H, d, 7.2 Hz), 3.96-4.01 (2H, m), 3.72 (1H, td, 11.1 Hz, 2.2 Hz), 3.52 (1H, d, 13.1 Hz), 3.32 (1H, d, 13.1 Hz), 2.68 (2H, q, 7.7 Hz), 2.59 (2H, br d, 11.7 Hz), 2.06-2.21 (2H, m), 1.12 (3H, t, 7.2 Hz); LCMS (2.5 minute method) m/z 404 [M+H]+ @ Rt 1.49 min.

ii) (2R)-2-[(R)-[(2-ethylphenyl)thio](phenyl)methyl]morpholine hydrochloride

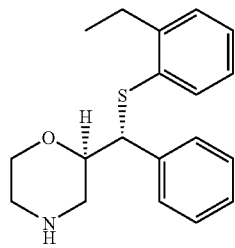

Reaction of (2S)-2-[(S)-[(2-ethylphenyl)thio](phenyl)methyl]4-(phenylmethyl)morpholine and (2R)-2-[(R)-[(2-ethylphenyl)thio](phenyl)methyl]-4-(phenylmethyl)morpholine following the method in example 1(iv) gave a viscous yellow oil (213.3 mg, 86% yield) from which the title product was obtained after chiral separation on chiral OD semi-preparative column; LC purity=100% (UV254 nm)/100% (ELS); MW 313.47; $C_{19}H_{23}NOS$; $^1H$ NMR (CDCl$_3$): 7.17 (1H, d, 7.6 Hz), 7.12-7.05 (5H, m), 7.01 (2H, d, 3.8 Hz), 6.87-6.93 (1H, m), 4.07 (1H, d, 8.1 Hz), 3.92-3.97 (1H, m), 3.74-3.80 (1H, m), 3.59 (1H, td, 11.4 Hz, 3.0 Hz), 2.80 (1H, td, 12.4 Hz, 3.3 Hz), 2.71 (1H, br. d, 12.1 Hz), 2.63-2.54 (4H, m), 1.64 (1H, br. s), 1.04 (3H, t, 7.6 Hz); LCMS (10 minutes method): m/z 314 [M+H]+ @ Rt 5.92 min. (2R)-2-[(R)-[(2-ethylphenyl)thio](phenyl)methyl]morpholine was converted into its hydrochloride salt. MW 349.93; $C_{19}H_{23}NOS.HCl$; $^1H$ NMR (CDCl$_3$): 10.10 (2H, br. s), 7.13-7.28 (8H, m), 7.02-7.08 (1H, m), 4.36 (1H, br. s), 4.01-4.17 (3H, br. m), 3.16-3.31 (2H, br. m), 2.92-3.09 (2H, br. m), 2.71 (2H, q, 7.7 Hz), 1.15 (3H, t, 7.2 Hz).

EXAMPLE 10

(2R)-2-[(R)-{[2-(Methyloxy)phenyl]thio}(phenyl)methyl]morpholine hydrochloride i) (2S)-2-[(S)-{[2-(Methyloxy)phenyl]thio}(phenyl)methyl]-4-(phenylmethyl)morpholine and (2R)-2-[(R)-{[2-(Methyloxy)phenyl]thio}(phenyl)methyl]-4-(phenylmethyl)morpholine

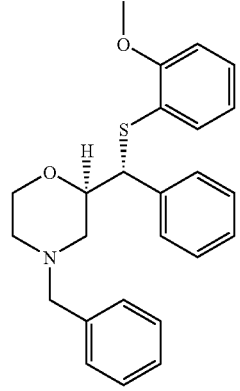

Compound (2S)-2-[(S)-{[2-(Methyloxy)phenyl]thio}(phenyl)methyl]-4-(phenylmethyl)morpholine and (2R)-2-[(R)-{[2-(Methyloxy)phenyl]thio}(phenyl)methyl]-4-(phenylmethyl)morpholine was obtained from 2-methoxy thiophenol (74 µl, 0.574 mmol) and (2R)-4-benzyl-2-[(S)-bromo(phenyl)methyl]morpholine and (2S)-4-benzyl-2-[(R)-bromo(phenyl)methyl]morpholine (181 mg, 0.522 mmol) following the method in example 8(vi) in which the reaction was heated at 95° C. for 2.5 h. After purification by flash column chromatography (eluent: ethyl acetate/hexane gradient 15/85 to 25/75 [v/v]) the product was obtained as a viscous yellow oil (175 mg, 83% yield); MW 405.56; $C_{25}H_{27}NO_2S$; $^1H$ NMR (CDCl$_3$): 7.01-7.26 (12H, m), 6.58-6.63 (2H, m), 4.39 (1H, d, 7.2 Hz), 3.86-3.91 (2H, m), 3.71 (3H, s), 3.56-3.62 (1H, m), 3.42 (1H, d, 10.8 Hz); 3.21 (1H, d, 10.8 Hz), 2.46-2.52 (2H, m), 2.01-2.11 (2H, m); LCMS (10 minutes method): m/z 406 [M+H]$^+$ @ $R_t$ 6.09 min.

ii) (2R)-2-[(R)-{[2-(Methyloxy)phenyl]thio}(phenyl)methyl]morpholine hydrochloride

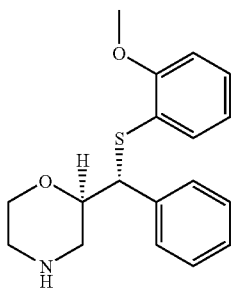

Reaction of (2S)-2-[(S)-{[2-(Methyloxy)phenyl]thio}(phenyl)methyl]-4-(phenylmethyl)morpholine and (2R)-2-[(R)-{[2-(Methyloxy)phenyl]thio}(phenyl)methyl]-4-(phenylmethyl)morpholine (100 mg, 0.25 mmol) following the method in example 1(iv) gave a viscous yellow oil (60 mg, 77% yield) from which the product was obtained after chiral separation on a Chiralcel OJ semi-preparative column. LC purity=100%; MW 315.44; $C_{18}H_{21}NO_2S$; $^1H$ NMR (CDCl$_3$): 7.14-7.34 (7H, m), 6.74-6.84 (2H, m), 4.50 (1H, d, 8.2 Hz), 4.10 (1H, d, 10.9 Hz), 3.85-4.00 (4H, m), 3.74 (1H, dt, 1.4 Hz, 11.3 Hz), 2.82-3.02 (2H, m), 2.66-3.02 (3H, m); LCMS (10 minutes method): 1m/z 316 [M+H]$^+$ @ R$_t$4.87 min. This was converted to its hydrochloride salt.

EXAMPLE 11

(2R)-2-[(R)-{[2-(methylthio)phenyl]thio}(phenyl)methyl]morpholine hydrochloride i) (2R)-2-((R)-[phenyl]{[2-methylthiophenyl]thio}methyl)-4-benzylmorpholine and (2S)-2-((S)-[phenyl]{[2-methylthiophenyl]thio}methyl)-4-benzylmorpholine

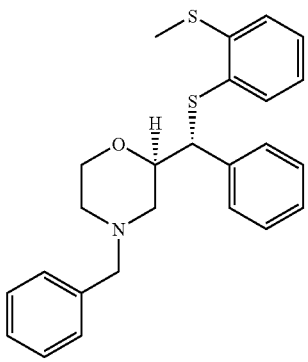

To a solution of (2R)-4-benzyl-2-[(S)-bromo(phenyl)methyl]morpholine and (2S)-4-benzyl-2-[(R)-bromo(phenyl)methyl]morpholine (4.0 g, 11.55 mmol) and 2-methylsulphenyl-thiophenol (1.2 eq, 2.17 g, 13.86 mmol) in anhydrous DMF (35 ml) at room temperature under nitrogen was added cesium carbonate (1.18 eq., 14.04 g, 13.63 mmol). The mixture was heated at 50° C. for 1.5 hours, allowed to cool to room temperature, taken up in methanol and treated with SCX-2 (100 g). The SCX-2 was washed with methanol. The product was obtained as a white solid (4.92 g) after SCX chromatography (eluent: ammonia/methanol 1/1 [v/v]) and removal of solvents in vacuo. Purification by flash column chromatography (eluent: ethyl acetate/isohexane gradient 10/90 to 30/70 [v/v]) gave a white solid (4.04 g, 86%); MW 421.63; $C_{27}H_{25}NOS_2$; $^1H$ NMR (CDCl$_3$): 7.03-7.15 (6H, m), 6.93-6.99 (2H, m), 6.74 (1H, td, 7.3 Hz, 1.5 Hz), 4.31 (1H, d, 7.8 Hz), 3.95 (1H, br. d, 12.1 Hz), 3.83 (1H, td, 8.1 Hz, 3.8 Hz), 3.59 (1H, td, 11.1 Hz, 2.8 Hz), 2.82 (1H, td, 12.1 Hz, 3.3 Hz), 2.61-2.75 (3H, m), 2.35 (3H, s), 1.73 (1H, br. s); LCMS (6 minutes method): m/z 422 [M+H]+ @ Rt 3.36 min.

ii) (2R)-2-[(R)-{[2-(methylthio)phenyl]thio}(phenyl)methyl]morpholine hydrochloride

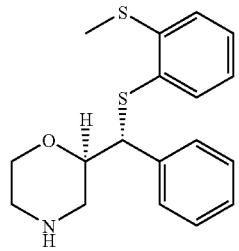

To a suspension of polymer supported Hunig's base (5.02 g) and (2R)-2-((R)-[phenyl]{[2-methylthiophenyl]thio}methyl)-4-benzylmorpholine and (2S)-2-((S)-[phenyl]{[2-methylthiophenyl]thio}methyl)-4-benzylmorpholine (4.02 g, 9.49 mmol) in dry dichloromethane (70 ml) was added α-chloroethyl chloroformate (2.93 ml, 28.6 mmol, 3 eq.) at room temperature and under nitrogen. The mixture was heated at 40° C. for 1.5 hours then left to stir at room temperature overnight. The reaction mixture was filtered and concentrated in vacuo to give a pale orange liquid. This was taken up in methanol (70 ml) and heated at 40° C. for 2 hours. A white solid crashed out of the solution which was purified by SCX chromatography (eluent: ammonia/methanol 1/1 [v/v]). After evaporation in vacuo the product was obtained as a pale yellow oil (3.13 g, 99%); MW 331.50; $C_{18}H_{21}NOS_2$; $^1H$ NMR (CDCl$_3$): 7.03-7.15 (6H, m), 6.93-6.99 (2H, m), 6.74 (1H, td, 7.3 Hz, 1.5 Hz), 4.31 (1H, d, 7.8 Hz), 3.95 (1H, br. d, 12.1 Hz), 3.83 (1H, td, 8.1 Hz, 3.8 Hz), 3.59 (1H, td, 11.1 Hz, 2.8 Hz), 2.82 (1H, td, 12.1 Hz, 3.3 Hz), 2.61-2.75 (3H, m), 2.35 (3H, s), 1.73 (1H, br. s). After separation by chiral chromatography the oil was converted into its hydrochloride salt in which the pale yellow oil was taken up in isopropanol (~200 ml) and filtered. Addition of hydrogen chloride (19 ml of a 1M solution in diethyl ether, 19 mmol) gave a white precipitate to which further diethyl ether (~50 ml) was added. The solid was isolated by filtration, washed with diethyl ether give the hydrochloride salt of the title product as a white solid (3.03 g); MW 367.96; $C_{18}H_{22}ClNOS_2$; $^1H$ NMR (CDCl$_3$): 9.94 (2H, br. s), 7.06-7.18 (6H, m), 6.94-7.03 (2H, m), 6.78 (1H, t, 6.8 Hz), 4.24-4.32 (1H, m), 4.20 (1H, d, 5.8 Hz), 3.89-4.06 (2H, m), 3.18 (2H, br. t, 11.9 Hz), 2.99 (2H, br. s), 2.37 (3H, s); LCMS (10 minutes method): m/z 332 [M−C]+ @ Rt 5.07 min.

EXAMPLE 12

(2R)-2-((R)-[4-chlorophenyl]{[2-methoxyphenyl]thio}methyl)morpholine hydrochloride

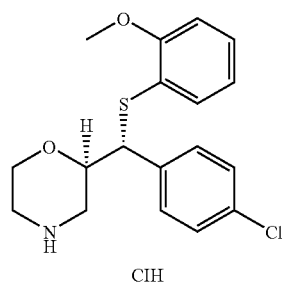

ClH

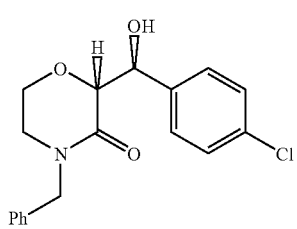

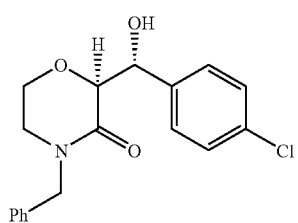

Diastereomer 1

A solution of lithium diisopropylanide (2M in heptane, 18.2 ml) was added dropwise over 20 min to a stirred solution of 4-benzyl-morpholin-3-one (5.0 g, 26 mmol) and 4-chlorobenzaldehyde (4.41 g, 31.4 mmol) in dried tetrahydrofuran (60 ml) cooled to −70° C. under nitrogen atmosphere. After 1 h at −70° C., the reaction mixture was quenched with aqueous ammonium chloride (100 ml) and extracted with ethyl acetate (100 ml). The extracts were washed with 2M aqueous hydrochloric acid (100 ml), brine solution (100 ml) and dried over sodium sulphate. After filtration, the solution was evaporated and the residual oil purified by chromatography on silica eluting with ethyl acetate:hexane 70:30 then ethyl acetate to give diastereomer 1 (2R)-2-[(S)-(4-chlorophenyl)(hydroxy)methyl]-4-benzyl-morpholin-3-one and (2S)-2-[(R)-(4-chlorophenyl)(hydroxy)methyl]-4-benzylmorpholin-3-one as a solid (2.64 g) followed by diastereomer 2 (2R)-2-[(R)-(4-chlorophenyl)(hydroxy)methyl]4-benzylmorpholin-3-one and (2S)-2-[(S)-(4-chlorophenyl)(hydroxy)methyl]-4-benzylmorpholin-3-one as an oil (1.46 g). Diastereomer 1 was recrystallised from ethyl acetate (25 ml) n-hexane (100 ml) to give white needles (2.47 g, 29%)

ii)

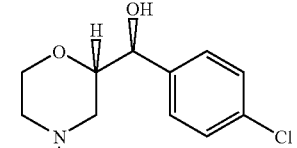

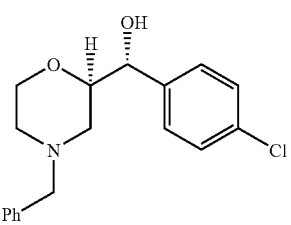

i)

A solution of borane in tetrahydrofuran (1M, 29 ml) was added dropwise to a stirred solution of diastereomer 1 (2R)-2-[(S)-(4-chlorophenyl)(hydroxy)methyl]-4-benzyl-morpholin-3-one and (2S)-2-[(R)-(4-chlorophenyl)(hydroxy)methyl]-4-benzylmorpholin-3-one (2.40 g 7.24 mmol) in dried tetrahydrofuran (30 ml) at room temperature under nitrogen causing effervesence. The solution was heated to 60° C. for 2 h, allowed to cool to room temperature and excess borane quenched by adding methanol (14 ml) slowly. Aqueous hydrochloric acid (1M, 14 ml) was added, heated to 60° C. for 1 h and then evaporated to a white solid. Added saturated aqueous sodium carbonate (50 ml) and diethyl ether (50 ml) to dissolve the solid and extracted with diethyl ether (2×50ml). The extracts were washed with brine solution, dried, filtered and evaporated to a colourless oil (2.38 g). The oil was purified by chromatography on silica eluting with diethyl ether:hexane 75:25 to give (R)-[4-chlorophenyl][(2R)-4-benzylmorpholin-2-yl]methanol and (S)-[4-chlorophenyl][(2S)-4-benzylmorpholin-2-yl]methanol as a colourless oil (2.08 g)

iii)

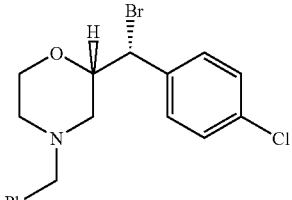

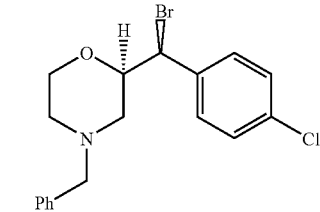

A solution of carbon tetrabromide (2.82 g, 8.5 mmol) in dichloromethane (3 ml) was added dropwise over 10 min to a stirred solution of (R)-[4-chlorophenyl][(2R)-4-benzyl-morpholin-2-yl]methanol and (S)-[4-chlorophenyl][(2S)-4-benzylmorpholin-2-yl]methanol (1.80 g, 5.67 mmol) and triphenylphosphine (2.23 g, 8.5 mmol) in dichloromethane (40 ml) at room temperature under nitrogen. After 30 min, the reaction solution was washed with saturated aqueous sodium bicarbonate (50 ml). The dichloromethane layer was dried, filtered and evaporated to a red liquid (8.5 g). Trituration with diethyl ether (20 ml) crystallised triphenylphoshine oxide that was then removed by filtration. The filtrate was evaporated to a yellow oil and was purified by chromatography on silica eluting with ethyl acetate:hexane 20:80 to give a colourless oil of (2R)-2-[(S)-bromo(4-chlorophenyl)methyl]-4-benzylmorpholine and (2S)-2-[(R)-bromo(4-chlorophenyl)methyl]-4-benzylmorpholine (1.17 g) that crystallised to a pink solid on standing.

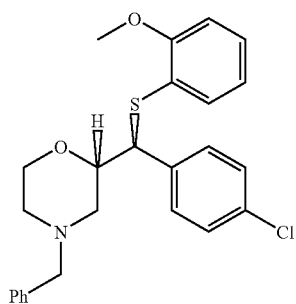

iv)

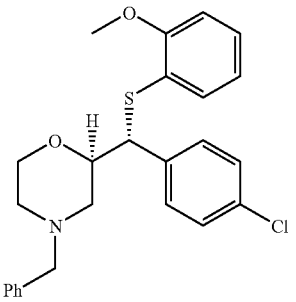

Cesium carbonate (667 mg, 2.05 mmol) was added to a stirred solution of (2R)-2-[(S)-bromo(4-chlorophenyl)methyl]-4-benzylmorpholine and (2S)-2-[(R)-bromo(4-chlorophenyl)methyl]-4-benzylmorpholine (651 mg, 1.71 mmol) and 2-methoxybenzenethiol (287 mg, 2.05 mmol) in dry dimethylformamide (3 ml). The suspension was heated to 90° C. for 1 h. The cooled reaction mixture was diluted with iced water, 2M aqueous sodium hydroxide (1 ml) and extracted with diethyl ether (15 ml). The extracts were washed with brine solution, dried, filtered and evaporated to a yellow oil (0.89 g). The crude product was purified by chromatography on silica eluting with ethyl acetate:heptane 1:4 to give 2(R)-2-((R)-[4-chlorophenyl]{[2-methoxyphenyl]thio}methyl)-4-benzylmorpholine and 2(S)-2-((S)-[4-chlorophenyl]{[2-methoxyphenyl]thio}methyl)-4-benzylmorpholine as a pale yellow oil (619 mg, 82%)

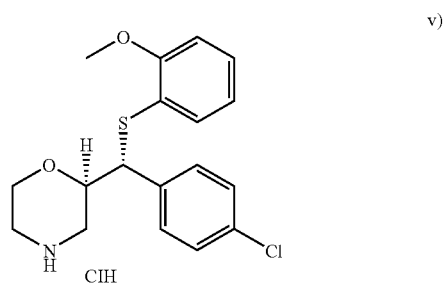

v)

Alpha-chloroethyl chloroformate (0.3 ml, 2.78 mmol) was added to a gently stirred suspension of polystyrene supported diisopropylethylamine (Argonaut, 390 mg, 1.39 mmol) and 2(R)-2-((R)-[4-chlorophenyl]{[2-methoxyphenyl]thio}methyl)-4-benzylmorpholine and 2(S)-2-((S)-[4-chlorophenyl]{[2-methoxyphenyl]thio}methyl)-4-benzylmorpholine (610 mg, 1.39 mmol) in dichloromethane (8 ml) at room temperature under nitrogen. After 3 h, the suspension was filtered and the filtrate evaporated. The residue was dissolved in methanol (10 ml) and heated to 60° C. for 1 h. The solution was evaporated and the solid residue crystallised from isopropanol (5 ml) diethyl ether (10 ml) to give a white solid (441 mg, 82%). The racemic hydrochloride salt was converted to the free base by stirring in dicloromethane (20 ml) and aqueous sodium hydroxide (1M, 20 ml). The dichloromethane layer was separated, dried, filtered and evaporated to a colourless oil (403 mg). Chiral preparative chromatography (Chiralcel-OD, heptane:ethanol:dimethylethylamine 50:50:0.2) was used to isolate the first eluting enantiomer Rt 9.3 min as an oil. This was redissolved in diethylether and treated with ethereal hydrogen chloride to give the title product (2R)-2-((R)-[4-chlorophenyl]{[2-methoxyphenyl]thio}methyl)morpholine hydrochloride as a solid (159 mg, 36%, mp 238-241° C.), NMR (DMSO) 9.31 (2H, br. s), 7.32 (4H, dd), 7.07-7.20 (2H, m), 6.91 (1H, d), 6.76 (1H, t), 4.67 (1H, d), 4.0-4.1 (2H, br d), 3.78 (3H, s), 3.72 (1H, t), 3.15 (1H, d), 2.95-3.1 (3H, m) LCMS: m/z 350 [M+H]+ @ Rt 3.8 min.

EXAMPLE 13

(2R)-2-((R)-[3-fluorophenyl]{[2-methoxyphenyl]thio}methyl)morpholine hydrochloride

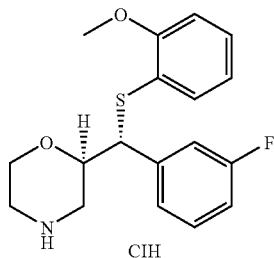

-continued

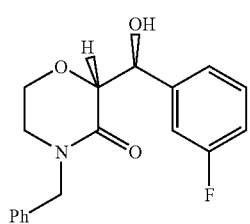

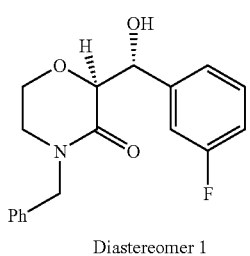

Diastereomer 1

A solution of lithium diisopropylamide (2M in heptane, 16.9 ml) was added dropwise over 15 min to a stirred solution of 4-benzyl-morpholin-3-one (5.0 g, 26 mmol) and 3-fluorobenzaldehyde (3.55 g, 28.6 mmol) in dried tetrahydrofuran (60 ml) cooled to −70° C. under nitrogen atmosphere. After 1 h at −70° C., the reaction mixture was quenched with aqueous ammonium chloride (100 ml) and extracted with ethyl acetate (100 ml). The extracts were washed with 2M aqueous hydrochloric acid (2×50 ml), brine solution (100 ml) and dried over sodium sulphate. After filtration, the solution was evaporated and the residual oil purified by chromatography on silica eluting with ethyl acetate:hexane 70:30 then ethyl acetate to give diastereomer 1 (2R)-2-[(S)-(3-fluorophenyl)(hydroxy)methyl]-4-benzyl-morpholin-3-one and (2S)-2-[(R)-(3-fluorophenyl)(hydroxy)methyl]-4-benzylmorpholin-3-one as a solid (3.8 g) followed by diastereomer 2 (2R)-2-[(R)-(3-fluorophenyl)(hydroxy)methyl]-4-benzylmorpholin-3-one and (2S)-2-[(S)-(3-fluorophenyl)(hydroxy)methyl]-4-benzylmorpholin-3-one as an oil (2.13 g). Diastereomer 1 was recrystallised from ethyl acetate (25 ml) n-hexane (100 ml) to give white needles (2.62 g, 32%).

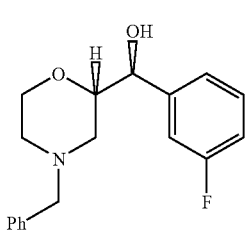

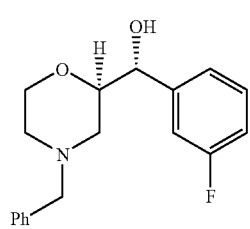

i)

A solution of borane in tetrahydrofuran (1M, 30.7 ml) was added dropwise to a stirred solution of diastereomer 1 (2R)-2-[(S)-(3-fluorophenyl)(hydroxy)methyl]-4-benzyl-morpholin-3-one and (2S)-2-[(R)-(3-fluorophenyl)(hydroxy)methyl]-4-benzylmorpholin-3-one (2.42 g 7.68 mmol) in dried tetrahydrofuran (30 ml) at room temperature under nitrogen causing effervesence. The solution was heated to 60° C. for 2 h, allowed to cool to room temperature and excess borane quenched by adding methanol (15 ml) slowly. Aqueous hydrochloric acid (1M, 15 ml) was added, heated to 60° C. for 1 h and then evaporated to a white solid. Added saturated aqueous sodium carbonate (50 ml) and diethyl ether (50 ml) to dissolve the solid and extracted with diethyl ether (2×50 ml). The extracts were washed with brine solution, dried, filtered and evaporated to a colourless oil (2.38 g). The oil was purified by chromatography on silica eluting with diethyl ether:hexane 75:25 to give (R)-[3-fluorophenyl][(2R)-4-benzylmorpholin-2-yl]methanol and (S)-[3-fluorophenyl][(2S)-4-benzylmorpholin-2-yl]methanol as a colourless oil (2.23 g)

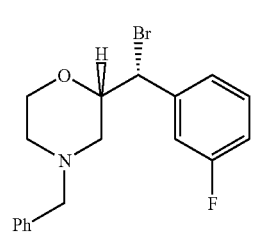

iii)

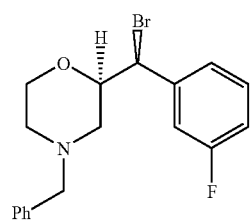

ii)

A solution of carbon tetrabromide (3.3 g, 9.96 mmol) in dichloromethane (4 ml) was added dropwise over 5 min to a stirred solution of (R)-[3-fluorophenyl][(2R)-4-benzyl-morpholin-2-yl]methanol and (S)-[3-fluorophenyl][(2S)-4-benzylmorpholin-2-yl]methanol (2.0 g, 6.64 mmol) and triphenylphosphine (2.61 g, 9.96 mmol) in dichloromethane (40 ml) at room temperature under nitrogen. After 30 min, the reaction solution was washed with saturated aqueous sodium bicarbonate (50 ml). The dichloromethane layer was dried, filtered and evaporated to a red liquid (8.5 g). Trituration with diethyl ether (40 ml) crystallised triphenylphoshine oxide that was then removed by filtration. The filtrate was evaporated to a yellow oil and was purified by chromatography on silica eluting with ethyl acetate:hexane 20:80 to give a colourless oil of (2R)-2-[(S)-bromo(3-fluorophenyl)methyl]-4-benzylmorpholine and (2S)-2-[(R)-bromo(3-fluorophenyl)methyl]-4-benzylmorpholine (0.811 g, 34%).

iv)

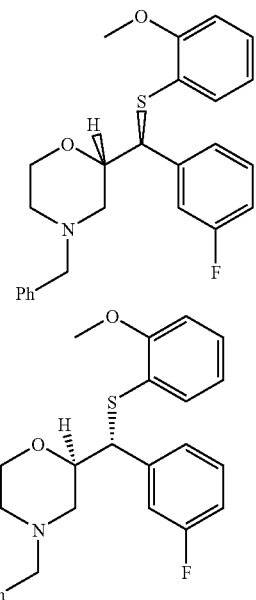

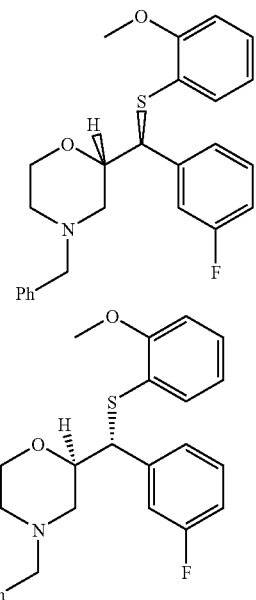

Cesium carbonate (546 mg, 1.68 mmol) was added to a stirred solution of (2R)-2-[(S)-bromo(3-fluorophenyl)methyl]-4-benzylmorpholine and (2S)-2-[(R)-bromo(3-fluorophenyl)methyl]-4-benzylmorpholine (510 mg, 1.4 mmol) and 2-methoxybenzenethiol (235 mg, 1.68 mmol) in dry dimethylformamide (3 ml). The suspension was stirred at room temperature for 4 h. The reaction mixture was diluted with iced water, 2M aqueous sodium hydroxide (1 ml) and extracted with diethyl ether (15 ml). The extracts were washed with brine solution, dried, filtered and evaporated to a yellow oil (627 mg). The crude product was purified by chromatography on silica eluting with ethyl acetate:heptane 20:80 to give 2(R)-2-((R)-[3-fluorophenyl]{[2-methoxyphenyl]thio}methyl)-4-benzylmorpholine and 2(S)-2-((S)-[3-fluorophenyl]{[2-methoxyphenyl]thio}methyl)-4-benzylmorpholine as a pale yellow oil (466 mg, 79%)

v)

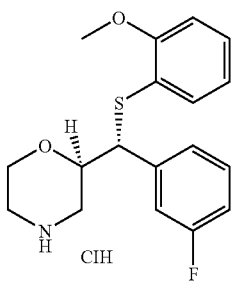

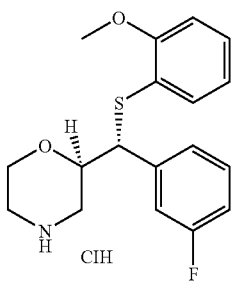

Alpha-chloroethyl chloroformate (0.235 ml, 2.17 mmol) was added to a gently stirred suspension of polystyrene supported diisopropylethylamine (Argonaut, 306 mg, 1.09 mmol) and 2(R)-2-((R)-[3-fluorophenyl]{[2-methoxyphenyl]thio}methyl)-4-benzylmorpholine and 2(S)-2-((S)-[3-fluorophenyl]{[2-methoxyphenyl]thio}methyl)-4-benzylmorpholine (460 mg, 1.09 mmol) in dichloromethane (6 ml) at room temperature under nitrogen. After 16 h, the suspension was filtered and the filtrate evaporated. The residue was dissolved in methanol (6 ml) and heated to 60° C. for 1 h. The solution was evaporated and the solid residue crystallised from isopropanol (15 ml) and n-hexane to give a white solid (371 mg, 92%). The racemic hydrochloride salt was converted to the free base by stirring in dicloromethane (20 ml) and aqueous sodium hydroxide (0.5M, 20 ml). The dichloromethane layer was separated, dried, filtered and evaporated to a colourless oil (341 mg). Chiral preparative chromatography (Chiralcel-OD, heptane:ethanol:dimethylethylamine 50:50:0.2) was used to isolate the first eluting enantiomer Rt 9.2 min as an oil. This was redissolved in diethylether and treated with ethereal hydrogen chloride to give the title product (2R)-2-((R)-[3-fluorophenyl]{[2-methoxyphenyl]thio}methyl)morpholine hydrochloride as a solid (138 mg, 34%, mp 233-234° C.). NMR (DMSO) 9.26 (2H, br. s), 7.31 (1H, q), 7.10-7.20 (4H, m), 7.05 (1H, t), 6.92 (1H, d), 6.78 (1H, t), 4.66 (1H, d), 4.0-4.15 (2H, m), 3.77 (3H, s), 3.72 (1H, t), 3.19 (1H, d), 2.92-3.1 (3H, m). LCMS: m/z 334 [M+H]$^+$ @ Rt 3.5 min

EXAMPLE 14

(2R)-2-((R)-[3-fluorophenyl]{[2-ethoxyphenyl]thio}methyl)morpholine hydrochloride Method 1

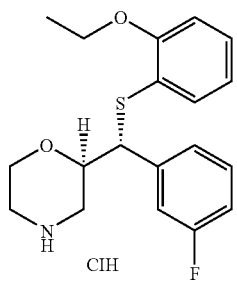

i)

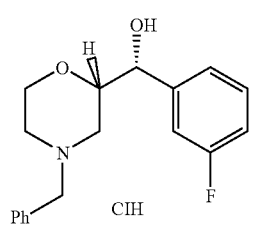

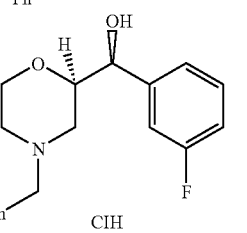

A solution of borane in tetrahydrofuran (1M, 25.2 ml) was added dropwise to a stirred solution of diastereomer 2 from example 13(i) (2R)-2-[(R)-(3-fluorophenyl)(hydroxy)methyl]-4-benzylmorpholin-3-one and (2S)-2-[(S)-(3-fluorophenyl)(hydroxy)methyl]-4-benzylmorpholin-3-one (2.0 g 6.3 mmol) in dried tetrahydrofuran (25 ml) at room temperature under nitrogen causing effervesence. The solution was heated to 60° C. for 1.5 h, allowed to cool to room temperature and excess borane quenched by adding methanol (10 ml) slowly. Aqueous hydrochloric acid (1M, 13 ml)

was added, heated to 60° C. for 1 h and then evaporated to a white solid. Added saturated aqueous sodium carbonate (50 ml) and diethyl ether (50 ml) to dissolve the solid and extracted with diethyl ether (2×50 ml). The extracts were washed with brine solution, dried, filtered and evaporated to a colourless oil (2.01 g). The oil was dissolved in isopropanol (20 ml) and ethereal hydrogen chloride (2M, 3 ml) added to crystallise the salt (R)-[3-fluorophenyl][(2S)-4-benzylmorpholin-2-yl]methanol hydrochloride and (S)-[3-fluorophenyl][(2R)-4-benzylmorpholin-2-yl]methanol hydrochloride as a white solid (1.66 g, 78%)

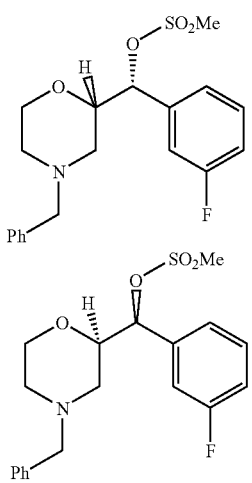

ii)

Methanesulphonyl chloride (1.01 g, 8.9 mmol) was added dropwise over 5 min to a stirred solution of (R)-[3-fluorophenyl][(2S)-4-benzylmorpholin-2-yl]methanol hydrochloride and (S)-[3-fluorophenyl][(2R)-4-benzylmorpholin-2-yl]methanol hydrochloride (1.50 g, 4.44 mmol) and triethylamine (1.79 g, 17.8 mmol) in dry dichloromethane (30 ml) at room temperature under nitrogen atmosphere. After 1 h, water (30 ml) was added, stirred vigorously and then the dichloromethane layer separated. The solution was dried over sodium sulphate, filtered and evaporated to a colourless oil. The oil was purified by chromatography on silica eluting with diethyl ether:hexane 3:1 to give (R)-[3-fluorophenyl][(2S)4-benzylmorpholin-2-yl]methyl methanesulphonate and (S)-[3-fluorophenyl][(2R)-4-benzylmorpholin-2-yl]methyl methanesulphonate as a colourless oil (1.51 g, 90%)

iii)

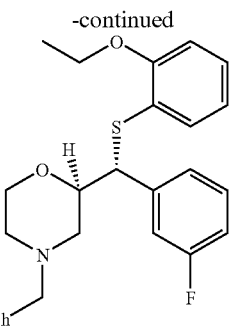

-continued

Anhydrous potassium carbonate (276 mg, 2 mmol) was added to a stirred solution of (R)-[3-fluorophenyl][(2S)-4-benzylmorpholin-2-yl]methyl methanesulphonate and (S)-[3-fluorophenyl][(2R)-4-benzylmorpholin-2-yl]methyl methanesulphonate (682 mg, 1.8 mmol) and 2-ethoxybenzenethiol (308 mg, 2 mmol) in dry dimethylformamide (13 ml) at room temperature under nitrogen atmosphere. After 3 days, water (25 ml) was added and the mixture extracted with diethyl ether (25 ml). The extracts were washed with brine solution (20 ml), dried, filtered and evaporated to a yellow oil (0.89 g). The product was purified by chromatography on silica eluting with ethyl acetate:heptane 20:80 to give 2(R)-2-((R)-[3-fluorophenyl]{[2-ethoxyphenyl]thio}methyl)-4-benzylmorpholine and 2(S)-2-((S)-[3-fluorophenyl]{[2-ethoxyphenyl]thio}methyl)-4-benzylmorpholine as a colourless oil (493 mg, 63%).

iv)

Debenzylation of 2(R)-2-((R)-[3-fluorophenyl]{[2-ethoxyphenyl]thio}methyl)-4-benzylmorpholine and 2(S)-2-((S)-[3-fluorophenyl]{[2-ethoxyphenyl]thio}methyl)-4-benzylmorpholine (480 mg, 1.1 mmol) using the method described in example 13(v) gave the racemic hydrochloride salt (360 mg, 85%). After conversion to the free base, chiral preparative chromatography (Chiralcel-OD, heptane:ethanol:dimethylethylamine 80:20:0.2) was used to isolate the first eluting enantiomer Rt 14.9 min as an oil. This was redissolved in diethylether and treated with ethereal hydrogen chloride to give the title product (2R)-2-((R)-[3-fluorophenyl]{[2-ethoxyphenyl]thio}methyl)morpholine hydrochloride as a solid (144 mg, 34%, mp 211-215° C.). NMR (DMSO) 9.30 (2H, br. s), 7.31 (1H, q), 7.11-7.20 (4H, m), 7.05 (1H, t), 6.91 (1H, d), 6.79 (1H, t), 4.64 (1H, d), 3.97-4.15 (4H, m), 3.72 (1H, t), 3.19 (1H, d), 2.92-3.1 (3H, m), 1.37 (3H, t). LCMS: m/z 348 [M+H]+ @ Rt 4.1 min Method 2 i)

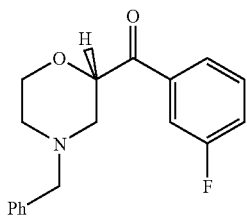

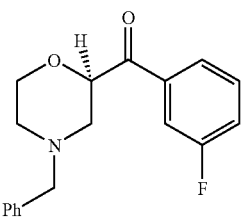

A solution of 3-fluorophenylmagnesium bromide (0.5M, 50 ml, 25 mmol) was added dropwise to a stirred solution of 4-benzyl-mopholin-2-carbonitrile (4.59 g, 22.7 mmol) in diethyl ether (50 ml) at 0° C. under nitrogen. After 45 min at 0 C. the mixture was allowed to warm to room temperature for 30 min then recooled and quenched by the addition of aqueous hydrochloric acid (5M, 40 ml)—caution exothermic. After 30 min at room temperature, the acidic mixture was basified with sodium hydroxide (5M, 60 ml) and extracted with ethyl acetate (3×150 ml). The combined extracts were washed with brine solution, dried, filtered and concentrated in vacuo to give (+/−)-(4-benzyl-morpholin-2-yl)-(3-fluorophenyl)methanone (6.9 g) as a yellow oil.

ii)

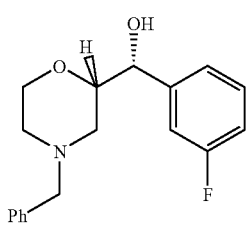

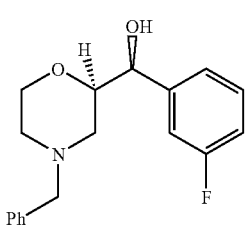

Borontrifluoride etherate (27.6 g, 194 mmol) followed by trifluoroacetic acid (40 ml) were added to a stirred solution of (+/−)-(4-benzyl-morpholin-2-yl)-(3-fluorophenyl)methanone (23.28 g, 77 mmol) and triphenylsilane (81.1 g, 311 mmol) in dichloromethane (1000 ml) at 0° C. under nitrogen. After 16 h at room temperature, reaction mixture was cooled and carefully basified by addition of aqueous sodium bicarbonate. The organic layer was separated, dried and concentrated in vacuo. The residual orange oil was purified using SCX-2 resin to absorb the amine product. Elution with methanolic ammonia (2M) and concentration in vacuo gave an oil (30 g) that was further purified by chromatography on silica (toluene:diethyl ether 60:40) to give (R)-[3-fluorophenyl][(2S)-4-benzylmorpholin-2-yl]methanol and (S)-[3-fluorophenyl][(2R)-4-benzylmorpholin-2-yl]methanol as an oil (19.7 g, 84%).

iii)

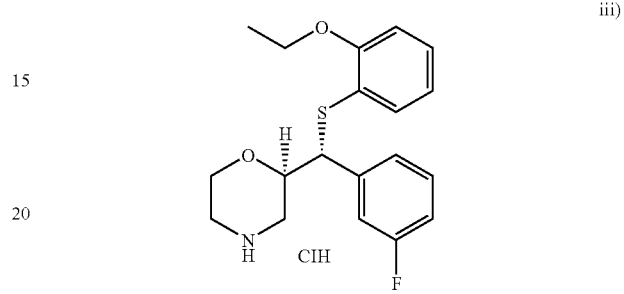

Convertion of (R)-[3-fluorophenyl][(2S)-4-benzylmorpholin-2-yl]methanol and (S)-[3-fluorophenyl][(2R)-4-benzylmorpholin-2-yl]methanol (19.7 g) using method 1 in example 14(ii) gave (R)-[3-fluorophenyl][(2S)-4-benzylmorpholin-2-yl]methyl methanesulphonate and (S)-[3-fluorophenyl][(2R)-4-benzylmorpholin-2-yl]methyl methanesulphonate (24.7 g) was followed by method 1 in example 14(iii) to give 2(R)-2-((R)-[3-fluorophenyl]{[2-ethoxyphenyl]thio}methyl)-4-benzylmorpholine and 2(S)-2-((S)-[3-fluorophenyl]{[2-ethoxyphenyl]thio}methyl)-4-benzylmorpholine (22.5 g). This was debenzylated by method 1 in example 14(iv) to give (2R)-2-((R)-[3-fluorophenyl]{[2-ethoxyphenyl]thio}methyl)morpholine and (2S)-2-((S)-[3-fluorophenyl]{[2-ethoxyphenyl]thio}methyl)morpholine (15.2 g) followed by preparative chiral chromatography to separate the first eluting enantiomer (7.7 g) and then salt formation to the title product (2R)-2-((R)-[3-fluorophenyl]{[2-ethoxyphenyl]thio}methyl)morpholine hydrochloride (4.38 g) as a white crystalline solid.

EXAMPLE 15

(2R)-2-((R)-[3-fluorophenyl]{[2-chlorophenyl]thio}methyl)morpholine hydrochloride

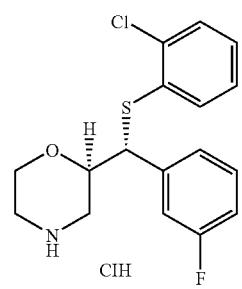

-continued

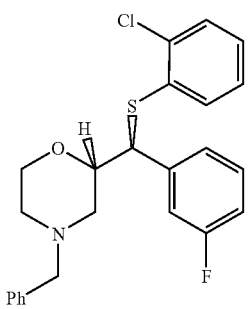

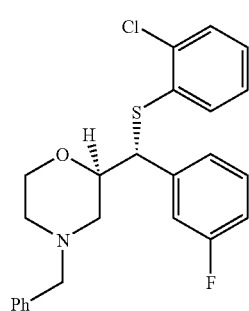

Anhydrous potassium carbonate (377 mg, 2.73 mmol) was added to a stirred solution of (R)-[3-fluorophenyl][(2S)-4-benzylmorpholin-2-yl]methyl methanesulphonate and (S)-[3-fluorophenyl][(2R)-4-benzylmorpholin-2-yl]methyl methanesulphonate (740 mg, 1.8 mmol) and 2-chlorobenzenethiol (393 mg, 2.73 mmol) in dry dimethylformamide (10 ml) at room temperature under nitrogen atmosphere. After 44 h, diluted with methanol (15 ml) and the inorganic solid filtered. The filtrate was poured directly onto SCX-2 columns (3×10 g), washed with methanol and the basic product eluted with methanolic ammonia (2M) to give a yellow oil (707 mg) after evaporation. The product was further purified by chromatography on silica eluting with ethyl acetate:heptane 20:80 to give 2(R)-2-((R)-[3-fluorophenyl]{[2-chlorophenyl]thio}methyl)-4-benzylmorpholine and 2(S)-2-((S)-[3-fluorophenyl]{[2-chlorophenyl]thio}methyl)-4-benzylmorpholine as a colourless oil (653 mg, 78%).

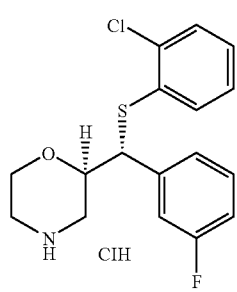

Alpha-chloroethyl chloroformate (0.33 ml, 3.06 mmol) was added to a gently stirred suspension of polystyrene supported diisopropylethylamine (Argonaut, 429 mg, 1.53 mmol) and 2(R)-2-((R)-[3-fluorophenyl]{[2-chlorophenyl]thio}methyl)-4-benzylmorpholine and 2(S)-2-((S)-[3-fluorophenyl]{[2-chlorophenyl]thio}methyl)-4-benzylmorpholine (429 mg, 1.53 mmol) in dichloromethane (10 ml) at room temperature under nitrogen. After 2 h, the suspension was filtered and the filtrate evaporated. The residue was dissolved in methanol (10 ml) and heated to 60° C. for 1 h. The solution was evaporated to the hydrochloride salt, redissolved in methanol and converted to the free base using SCX-2 column (10 g) eluting with methanol and then methanolic ammonia (2M) to give a colourless oil (501 mg, 97%). Chiral preparative chromatography (Chiralcel-OJ, heptane:isopropanol:dimethylethylamine 90:10:0.2) was used to isolate the first eluting enantiomer Rt 19.2 min as an oil. This was redissolved in diethylether and treated with ethereal hydrogen chloride to give the title product (2R)-2-((R)-[3-fluorophenyl]{[2-chlorophenyl]thio}methyl)morpholine hydrochloride as a solid (231 mg, 40%, mp 183-7° C.). NMR (DMSO) 9.38 (2H, br. s), 7.15-7.47 (7H, m), 7.09 (1H, t), 4.85 (1H, d), 4.12-4.20 (1H, m), 4.08 (1H, d), 3.77 (1H, t), 3.20 (1H, d), 2.95-3.10 (3H, m). LCMS: m/z 338/340 [M+H$^+$ @ Rt 3.9 min

EXAMPLE 16

(2R)-2-[(R)-(2-chloro-6-methylphenyl)thio](phenyl)methyl]morpholine hydrochloride

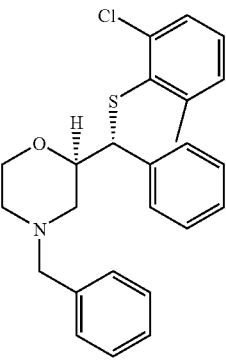

To a solution of (2R)-4-benzyl-2[(S)-bromo(phenyl)methyl]morpholine (200 mg, 0.6 mmol) and 2-chloro-6-methyl thiophenol (0.167 ml, 6 eq) in anhydrous DMF (5 ml) at room temperature under nitrogen was added potassium carbonate (100 mg, 0.7 mmol, 1.2 eq). The reaction mixture was stirred at room temperature for 5 hours. The reaction mixture was diluted with methanol and poured directly onto a SCX-2 column for purification to give (2R)-2-[(R)-(2-chloro-6-methylphenyl)thio](phenyl)methyl]-4-(phenyl)methyl]morpholine before taking directly onto the next step.

ii) (2R)-2-[(R)-(2-chloro-6 methylphenyl)thio](phenyl)methyl]morpholine hydrochloride

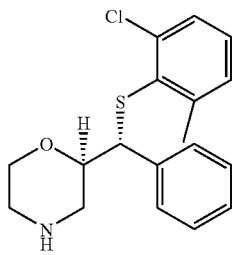

To a suspension of polymer supported Hunig's base (182 mg, 3 eq) and (2R)-2-[(R)-(2-chloro-6 methylphenyl)thio](phenyl)methyl]-4-(phenyl)methyl]morpholine (254 mg, 0.6 mmol) in dry DCM (5 ml) was added α-chloroethyl chloroformate (0.187 ml, 1.7 mmol, 3 eq) at room temperature and under nitrogen. The mixture was allowed to stir at room temperature overnight. The reaction mixture was taken up in methanol (5 ml) and stirred at room temperature overnight. The reaction mixture was then treated with SCX-2 (10 g). After elution with methanol followed by elution with 7 N $NH_3$/methanol (2R)-2-[(R)-(2-chloro-6 methylphenyl)thio](phenyl)methyl]morpholine was obtained as an oil (163 mg, 82% yield); MW 333; $C_{18}H_{20}ClNOS$; $^1H$ NMR (DMSO): 8.80 (1H, br s), 7.30 (1H, m), 7.20 (7H, m), 4.40 (1H, d, 8.2 Hz), 4.20 (1H, m), 4.00 (1H, m), 3.80 (1H, m), 3.15 (1H, m), 2.90 (2H, m), 2.20 (3H, s) 1.20 (1H, m); LCMS (10 minutes method): m/z 334[M+H]$^+$ @ $R_T$5.1 min; HPLC purity=100% ($UV_{215nm}$)/100% (ELS). The free base was converted into the title product HCl salt.

EXAMPLE 17

(2R)-2-((R)-[4-fluorophenyl]{2-methoxyphenyl]thio}methyl)morpholine hydrochloride

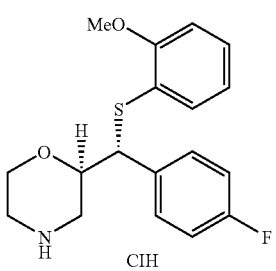

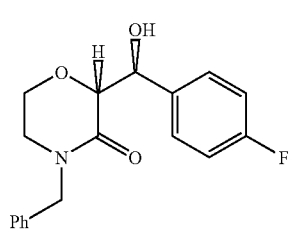

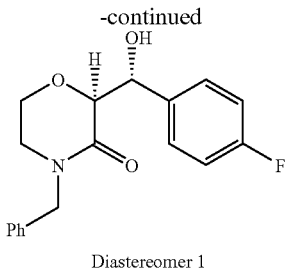

Diastereomer 1

Following the procedure described in example 5(i), 4-benzylmorpholin-3-one (4.06 g) was converted to 2-(R)-2-[(S)-(4-fluorphenyl)(hydroxy)methyl]-4-benzylmorpholin-3-one and 2-(S)-2-[(R)-(4-fluorophenyl)(hydroxy)methyl]-4-benzylmorpholin-3-one. Crystallised from hexane-ethyl acetate to give a colourless solid (2.04 g).

ii)

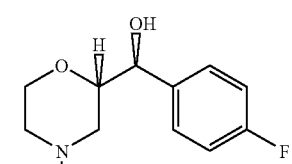

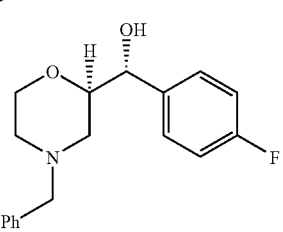

2-(R)-2-[(S)-(4-fluorophenyl)(hydroxy)methyl]-4-benzylmorpholin-3-one and 2-(S)-2-[(R)-(4-fluorophenyl)(hydroxy)methyl]-4-benzylmorpholin-3-one (2.0 g) was converted to (R)-[4-fluorophenyl][(2R)-4-benzylmorpholin-2-yl]methanol and (S)-[4-fluorophenyl][(2S)-4-benzylmorpholin-2-yl]methanol following procedure described in example 2(ii) to give a colourless oil (1.88 g).

iii)

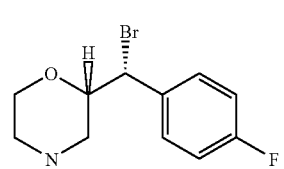

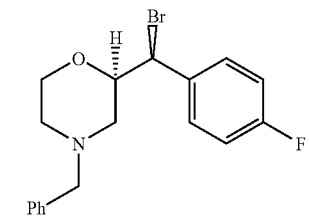

To a stirred solution of (R)-[4-fluorophenyl][(2R)-4-benzylmorpholin-2-yl]methanol and (S)-[4-fluorophenyl][(2S)-4-benzylmorpholin-2-yl]methanol (1.64 g, 5.54 mmol)) and triphenylphosphine (2.32 g, 8.86 mmol) in anhydrous chloroform (40 ml) was added solid carbon tetrabromide (2.76 g, 8.31 mmol) in one lot. The solution was heated at reflux under nitrogen for 3 h. Cooled and washed reaction mixture with brine, dried, filtered and evaporated to a red oil. The oil was purified by chromatography on silica eluting with hexane:ethyl acetate 41:9 to give 2(R)-2-[(S)-bromo(4-fluorophenyl)methyl]-4-benzylmorpholine and 2(S)-2-[(R)-bromo(4-fluorophenyl)methyl]-4-benzylmorpholine as a colourless oil (0.49 g)

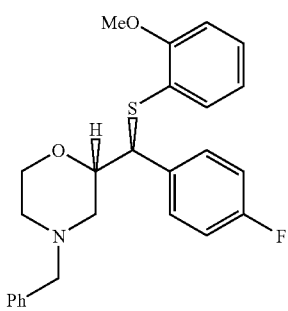

iv)

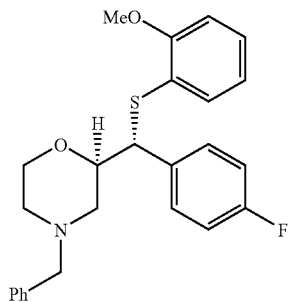

To a stirred suspension of 2(R)-2-[(S)-bromo(4-fluorophenyl)methyl]-4-benzylmorpholine and 2(S)-2-[(R)-bromo(4-fluorophenyl)methyl]-4-benzylmorpholine (0.6 g, 1.65 mmol) and cesium carbonate (0.59 g, 1.81 mmol) in dry DMF (5 ml) was added 2-methoxybenzenethiol (0.25 g, 1.81 mmol). The suspension was heated at 90° C. under nitrogen for 3 h. The cooled reaction mixture was diluted with water and extracted with diethyl ether. The extracts were washed with water and brine, dried, filtered and evaporated to an oil. The crude oil was purified by chromatography on silica eluting with hexane:ethyl acetate 4:1 then 3:2 to give (2R)-2-((R)-(4-fluorophenyl){[2-methoxyphenyl]thio}methyl)morpholine and (2S)-2-((S)-(4-fluorophenyl){[2-methoxyphenyl]thio}methyl)morpholine a colourless oil (0.22 g)

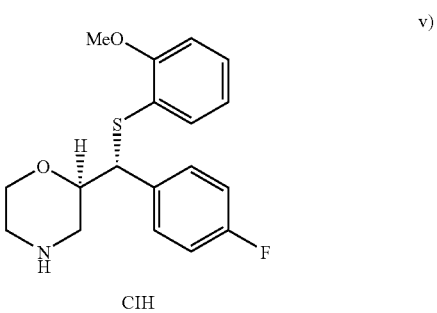

v)

CIH

Reaction of the mixture of (2R)-2-((R)-(4-fluorophenyl){[2-methoxyphenyl]thio}methyl)morpholine and (2S)-2-((S)-(4-fluorophenyl){[2-methoxyphenyl]thio}methyl)morpholine (430 mg, 1.02 mmol) following procedure described in EXAMPLE 1(iv) gave a colourless oil (340 mg, 90% yield) from which first eluting enantiomer (2R)-2-((R)-(4-fluorophenyl){[2-methoxyphenyl]thio}methyl)morpholine was obtained after chiral chromatography on a Chiralcel-OD column eluant heptane/isopropanol/dimethylethylamine (50/50/0.2): Rt 10.58 min. This was converted into its hydrochloride salt. $^1$H NMR (CD$_3$OD): 7.01-7.20 (4H, m), 6.70-6.80 (3H, m), 6.60 (1H, t), 4.37 (1H, d,), 3.82-3.90 (1H, m), 3.70-3.79 (4H, m), 3.49-3.60 (1H, m), 2.70-2.78 (2H, m),.2.60-2.70 (2H, m).

The pharmacological profile of the present compounds may be demonstrated as follows. All of the exemplified compounds above have been found to exhibit a $K_i$ value less than 100 nM at the serotonin transporter and a $K_i$ value less than 100 nM at the norepinephrine transporter as determined using the scintillation proximity assays described below. Furthermore, all of the exemplified compounds above have been found to selectively inhibit the serotonin and norepinephrine transporters relative to the dopamine transporter by a factor of at least five using the scintillation proximity assays as described below.

Generation of Stable Cell-lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganapathy V and Blakely R D. *Antidepressant- and cocaine-sensitive human serotonin transporter: Molecular cloning, expression, and chromosomal localization.* Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™—Invitrogen) following the manufacture's protocol.

Scintillation Proximity Assays for Determining the Affinity of Test Ligands at the Norepinephrine and Serotonin Transporters.

The compounds of the present invention are norepinephrine and serotonin reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus $^3$H-nisoxetine binding to norepinephrine re-uptake sites in a cell line transfected with DNA encoding human norepinephrine transporter binding protein and similarly $^3$H-citalopram binding to serotonin re-uptake sites in a cell line transfected with DNA encoding human serotonin transporter binding protein have been used to determine the affinity of ligands at the norepinephrine and serotonin transporters respectively.

Norepinephrine Binding Assay

Membrane Preparation:

Cell pastes from large scale production of HEK-293 cells expressing cloned human norepinephrine transporters were homogenized in 4 volumes 50 mM Tris-HCl containing 300 mM NaCl and 5 mM KCl, pH 7.4. The homogenate was centrifuged twice (40,000 g, 10 min, 4° C.) with pellet re-suspension in 4 volumes of Tris-HCl buffer containing the above reagents after the first spin and 8 volumes after the second spin. The suspended homogenate was centrifuged (100 g, 10 min, 4° C.) and the supernatant kept and re-centrifuged (40,000 g, 20 min, 4° C.). The pellet was resuspended in Tris-HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[$^3$H]-Nisoxetine Binding Assay:

Each well of a 96 well microtitre plate was set up to contain the following:

50 µl 2 nM [N-methyl-$^3$H]-Nisoxetine hydrochloride (70-87 Ci/mmol, from NEN Life Science Products)

75 µl Assay buffer (50 mM Tris-HCl pH 7.4 containing 300 mM NaCl and 5 mM KCl)

25 µl Test compound, assay buffer (total binding) or 10 µm Desipramine HCl (non-specific binding)

50 µl Wheatgerm agglutinin coated poly(vinyltoluene) (WGA PVT) SPA Beads (Amersham Biosciences RPNQ0001) (10 mg/ml)

50 µl Membrane (0.2 mg protein per ml)

The microtitre plates were incubated at room temperature for 10 hours prior to reading in a Trilux scintillation counter. The results were analysed using an automatic spline fitting programmed (Multicalc, Packard, Milton Keynes, UK) to provide Ki values for each of the test compounds.

Serotonin Binding Assay

The ability of a test compound to compete with [$^3$H]-citalopram for its binding sites on cloned human serotonin transporter containing membranes has been used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation was stored in aliquots (1 ml) at −70° C. until required. The protein concentration of the membrane preparation was determined using a BCA protein assay reagent kit.

[$^3$H]-Citalopram Binding Assay:

Each well of a 96 well microtitre plate was set up to contain the following:

50 µl 2 nM [$^3$H]-Citalopram (60-86 Ci/mmol, Amersham Biosciences)

75 µl Assay buffer (50 mM Tris-HCl pH 7.4 containing 150 mM NaCl and 5 mM KCl)

25 µl Diluted compound, assay buffer (total binding) or 100 µM Fluoxetine (non-specific binding)

50 µl WGA PVT SPA Beads (40 mg/ml)

50 µl Membrane preparation (0.4 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki (nM) values for each of the unknown compounds.

Dopamine Binding Assay

The ability of a test compound to compete with [$^3$H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[$^3$H]-WIN35,428 Binding Assay:

Each well of a 96well microtitre plate was set up to contain the following:

50 µl 4 nM [$^3$H]-WIN35,428 (84-87 Ci/mmol, from NEN Life Science Products)

75 µl Assay buffer (50 mM Tris-HCl pH 7.4 containing 150 mM NaCl and 5 mM KCl)

25 µl Diluted compound, assay buffer (total binding) or 100 µM Nomifensine (non-specific binding)

50 µl WGA PVT SPA Beads (10 mg/ml)

50 µl Membrane preparation (0.2 mg protein per ml.)

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the unknown compounds.

Formalin Paw Assay

The analgesic effect of compounds of the invention for the treatment of persistent nociceptive pain was demonstrated using the well-known "formalin test." The formalin test is a model of persistent nociceptive activation induced by tissue injury which can lead to central sensitization. (Shibata, M., Ohkubo, T., Takahashi, H., and Inoki, R., "Modified formalin test: Characteristic biphasic pain response," *Pain* (1989) 38: 347-352; and Tjolsen, A., Berge, O. G., Hunskaar, S., Rosland, J. H., and Hole, K., "The formalin test: an evaluation of the method," *Pain* (1992) 51:5-17. ) The effect of compounds of the invention on formalin-induced paw-licking behavior in the rat was investigated as an index of persistent nociceptive activation. In this test, the injection of formalin under the skin on the dorsal lateral surface of the hind paw of rats causes an immediate and intense increase in the spontaneous activity of C fiber afferents. This activation evokes a distinctly quantifiable behavior indicative of pain, such as licking of the injected paw. The behavioral response to formalin is biphasic, with an early phase that is short lived, followed by an extended tonic response or late phase of persistent nociceptive activation. Mechanisms causing the late phase response, such as central sensitization of pain transmitting neurons, are currently believed to contribute to various types of persistent pains.

Male Sprague-Dawley rats (200-250 g; Charles River, Portage, Mich.) were maintained at constant temperature and light (12 h light/12 h dark) for 4-7 days prior to the studies. Animals had free access to food and water at all times prior to the day of the experiment.

The formalin test was performed in custom made Plexiglas® boxes 25×25×20 cm (length×width×height) in size. A mirror placed at the back of the box allowed the unhindered observation of the formalin injected paw. Rats were acclimatized individually in the cubicles at least 1 hour prior to the experiment. All testing was conducted between 08:00 and 14:00 hr and the testing room temperature was maintained at 21-23° C. Test compound was administered 30 or 60 minutes prior to the formalin injection. Formalin (50 µl of a 5% solution in saline) was injected subcutaneously into the dorsal lateral surface of the right hind paw with a 27 gauge needle. Observation started immediately after the formalin injection. Formalin-induced pain was quantified by recording in 5 minute intervals the number of formalin injected paw licking events and the number of seconds each licking event lasted. These recordings were made for 50 minutes after the formalin injection. Scoring in the formalin test was performed according to Coderre et al., 1993b and Abbott et al., 1995. (Coderre T. J., Fundytus M. E., McKenna J. E., Dalal S. and Melzack R. "The formalin test: a validation of the weighted-scores method of the behavioral pain rating," *Pain*(1993b) 54: 43-50; and Abbott F. V., Franklin K. B. J. and Westbrook R. F. "The formalin test: scoring properties of the first and second phases of the pain response in rats," *Pain* (1995) 60: 91-102.) The sum of time spent licking in seconds from time 0 to 5 minutes was considered the early phase while the late phase was taken as the sum of seconds spent licking from 15 to 40 minutes.

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme shows a genetic polymorphism with as a consequence a presence in the population of poor and normal metabolizers. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhihibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the new chemical entity (NCE) was prepared in a mixture of Acetonitrile/Water to reach a final concentration of acetonitrile in the incubation below 0.5%.

The microsomal incubation mixture (total volume 0.1 mL) contained the NCE (4 µM), β-NADPH (1 mM), microsomal proteins (0.5 mg/mL), and Quinidine (0 or 2 µM) in 100 mM sodium phosphate buffer pH 7.4. The mixture was incubated for 30 minutes at 37° C. in a shaking waterbath. The reaction was terminated by the addition of acetonitrile (75 µL). The samples were vortexed and the denaturated proteins were removed by centrifugation. The amount of NCE in the supernatant was analyzed by liquid chromatography/mass spectrometry (LC/MS) after addition of an internal standard. A sample was also taken at the start of the incubation (t=0), and analysed similarly.

Analysis of the NCE was performed by liquid chromatography/mass spectrometry. Ten µL of diluted samples (20 fold dilution in the mobile phase) were injected onto a Spherisorb CN Column, 5 µM and 2.1 mm×100 mm (Waters corp. Milford, Mass., USA). The mobile phase consisting of a mixture of Solvent A/Solvent B, 30/70 (v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The NCE and the internal standard were quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(NCE \text{ response in samples without inhibitor})\text{time 0} - (NCE \text{ response in samples without inhibitor})\text{time 30}}{(NCE \text{ response in samples without inhibitor})\text{time 0}} \times 100$$

The extent of metabolism with inhibitor (%) was calculated as follows:

$$\frac{(NCE \text{ response in samples without inhibitor})\text{time 0} - (NCE \text{ response in samples without inhibitor})\text{time 30}}{(NCE \text{ response in samples without inhibitor})\text{time 0}} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 µM for CYP2D6 activity, the $IC_{50}$ being the concentration of the compound that gives 50% of inhibition of the CYP2D6 activity.

Material and methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine (Manchester, UK). All the other reagents and solvents were of analytical grade.

Microsomal incubation mixture (total volume 0.1 mL) contained bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture was incubated in a shaking waterbath at 37° C. for 5 minutes. The reaction was terminated by the addition of methanol (75 µL). The samples were vortexed and the denaturated proteins were removed by centrifugation. The supernatant was analyzed by liquid chromatography connected to a fluorescence detector. The formation of the 1'-hydroxybufuralol was monitored in control samples (0 µM NCE) and in the samples incubated in presence of the NCE. The stock solution of NCE was prepared in a mixture of Acetonitrile/Water to reach a final concentration of acetonitrile in the incubation below 1.0%.

The determination of 1' hydroxybufuralol in the samples was performed by liquid chromatograhy with fluorimetric detection as described below. Twenty five µL samples were injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ 252 nm and emission at λ 302 nm.

The $IC_{50}$ of the NCE for CYP2D6 was calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibition})}{\text{Percent of inhibition}}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

X-Ray Crystallographic Data

TABLE 1

Crystal data and structure refinement for 2003xf.

| | |
|---|---|
| Identification code | 2003xf |
| Empirical formula | C18H19ClF3NOS |
| Formula weight | 389.85 |
| Temperature | 107(2) K |
| Wavelength | 0.71073 Å |
| Crystal system, space group | Monoclinic, P2(1) |

TABLE 1-continued

Crystal data and structure refinement for 2003xf.

| | |
|---|---|
| Unit cell dimensions | a = 9.984(2) Å    alpha = 90 deg. |
| | b = 5.6484(13) Å    beta = 100.867(4) deg. |
| | c = 15.931(4) Å    gamma = 90 deg. |
| Volume | 882.4(4) Å$^3$ |
| Z, Calculated density | 2, 1.467 Mg/m$^3$ |
| Absorption coefficient | 0.371 mm$^{-1}$ |
| F(000) | 404 |
| Crystal size | .06 × .08 × .18 mm |
| Theta range for data collection | 1.30 to 28.20 deg. |
| Limiting indices | 11 <= h <= 13, -7 <= k <= 7, |
| | -20 <= l <= 19 |
| Reflections collected/unique | 5986/3378 [R(int) = 0.0661] |
| Completeness to theta = 28.20 | 92.9% |
| Absorption correction | None |
| Refinement method | Full-matrix least-squares on F$^2$ |
| Data/restraints/parameters | 3378/1/234 |
| Goodness-of-fit on F$^2$ | 0.846 |
| Final R indices [I > 2sigma(I)] | R1 = 0.0488, wR2 = 0.0908 |
| R indices (all data) | R1 = 0.1227, wR2 = 0.1101 |
| Absolute structure parameter | 0.11(10) |
| Largest diff. peak and hole | 0.548 and -0.444 e.Å$^{-3}$ |

X-Ray Crystallographic Data

TABLE 2

Atomic coordinates (×10$^4$) and equivalent isotropic displacement parameters (Å$^2$ × 10$^3$) for 2003xf.
U(eq) is defined as one third of the trace of the orthogonalized Uij tensor.

| | x | y | z | U(eq) |
|---|---|---|---|---|
| S(8) | 8641(1) | 5291(2) | 2641(1) | 35(1) |
| O(1) | 10279(3) | 2645(5) | 4200(2) | 24(1) |
| C(7) | 9992(5) | 3088(8) | 2678(3) | 25(1) |
| F(3) | 5136(4) | 4842(7) | 443(2) | 65(1) |
| N(4) | 13055(4) | 1352(9) | 4386(3) | 21(1) |
| C(5) | 12147(4) | 1431(8) | 3536(3) | 22(1) |
| F(2) | 7264(4) | 4253(5) | 644(2) | 51(1) |
| C(20) | 10490(5) | 1794(8) | 1263(3) | 31(1) |
| F(1) | 6497(4) | 7227(5) | 1228(2) | 48(1) |
| C(15) | 10669(5) | 3416(8) | 1925(3) | 24(1) |
| C(6) | 11008(5) | 3187(8) | 3525(3) | 24(1) |
| C(16) | 11472(5) | 5394(10) | 1846(3) | 32(1) |
| C(10) | 6184(5) | 3389(9) | 1805(3) | 26(1) |
| C(13) | 5978(5) | 382(11) | 3117(4) | 40(1) |
| C(9) | 7190(5) | 3438(9) | 2506(3) | 30(1) |
| C(3) | 12283(5) | 976(8) | 5085(3) | 27(1) |
| C(12) | 4992(5) | 364(10) | 2423(4) | 31(1) |
| C(2) | 11168(5) | 2787(9) | 5010(3) | 28(1) |
| C(21) | 6263(6) | 4934(11) | 1033(4) | 41(2) |
| C(18) | 11846(5) | 4080(10) | 494(3) | 33(1) |
| C(17) | 12048(5) | 5721(9) | 1131(4) | 36(1) |
| C(19) | 11078(5) | 2138(9) | 552(4) | 35(1) |
| C(11) | 5062(5) | 1943(9) | 1738(4) | 42(2) |
| C(14) | 7065(6) | 1852(10) | 3160(4) | 43(2) |
| Cl(1) | 4131(1) | 6360(2) | 4214(1) | 30(1) |

X-Ray Crystallographic Data

TABLE 3

Bond lengths [Å] and angles [deg] for 2003xf.

| | |
|---|---|
| S(8)—C(9) | 1.767(5) |
| S(8)—C(7) | 1.828(5) |
| O(1)—C(2) | 1.424(5) |
| O(1)—C(6) | 1.440(5) |
| C(7)—C(15) | 1.495(6) |
| C(7)—C(6) | 1.528(6) |
| F(3)—C(21) | 1.318(5) |
| N(4)—C(5) | 1.481(5) |
| N(4)—C(3) | 1.484(6) |
| C(5)—C(6) | 1.507(6) |
| F(2)—C(21) | 1.337(6) |
| C(20)—C(19) | 1.385(7) |
| C(20)—C(15) | 1.383(6) |
| F(1)—C(21) | 1.343(6) |
| C(15)—C(16) | 1.395(6) |
| C(16)—C(17) | 1.382(7) |
| C(10)—C(9) | 1.354(6) |
| C(10)—C(11) | 1.374(7) |
| C(10)—C(21) | 1.520(8) |
| C(13)—C(12) | 1.334(6) |
| C(13)—C(14) | 1.358(7) |
| C(9)—C(14) | 1.397(7) |
| C(3)—C(2) | 1.500(6) |
| C(12)—C(11) | 1.421(7) |
| C(18)—C(19) | 1.351(7) |
| C(18)—C(17) | 1.360(7) |
| C(9)—S(8)—C(7) | 100.6(2) |
| C(2)—O(1)—C(6) | 110.4(4) |
| C(15)—C(7)—C(6) | 112.3(4) |
| C(15)—C(7)—S(8) | 109.4(3) |
| C(6)—C(7)—S(8) | 111.5(3) |
| C(5)—N(4)—C(3) | 112.0(4) |
| N(4)—C(5)—C(6) | 11.2(4) |
| C(19)—C(20)—C(15) | 121.2(5) |
| C(20)—C(15)—C(16) | 117.1(5) |
| C(20)—C(15)—C(7) | 121.1(5) |
| C(16)—C(15)—C(7) | 121.8(5) |
| O(1)—C(6)—C(5) | 109.7(4) |
| O(1)—C(6)—C(7) | 107.9(4) |
| C(5)—C(6)—C(7) | 111.1(4) |
| C(17)—C(16)—C(15) | 121.2(5) |
| C(9)—C(10)—C(11) | 122.9(5) |
| C(9)—C(10)—C(21) | 121.0(5) |
| C(11)—C(10)—C(21) | 116.0(5) |
| C(12)—C(13)—C(14) | 120.3(6) |
| C(10)—C(9)—C(14) | 116.4(5) |
| C(10)—C(9)—S(8) | 125.2(4) |
| C(14)—C(9)—S(8) | 118.4(4) |
| N(4)—C(3)—C(2) | 109.0(4) |
| C(13)—C(12)—C(11) | 119.7(5) |
| O(1)—C(2)—C(3) | 111.1(4) |
| F(3)—C(21)—F(1) | 107.1(5) |
| F(3)—C(21)—F(2) | 105.6(5) |
| F(1)—C(21)—F(2) | 105.4(5) |
| F(3)—C(21)—C(10) | 113.2(5) |
| F(1)—C(21)—C(10) | 113.6(5) |
| F(2)—C(21)—C(10) | 111.4(5) |
| C(19)—C(18)—C(17) | 120.6(5) |
| C(18)—C(17)—C(16) | 119.8(5) |
| C(18)—C(19)—C(20) | 120.2(5) |
| C(10)—C(11)—C(12) | 118.1(5) |
| C(13)—C(14)—C(9) | 122.5(5) |

Symmetry transformations used to generate equivalent atoms:

X-Ray Crystallographic Data

TABLE 4

Anisotropic displacement parameters (Å$^2$ × 10$^3$) for 2003xf.
The anisotropic displacement factor exponent takes the form:
$-2\pi^2 [ h^2 a^{*2} U11 + \ldots + 2 h k a^* b^* U12 ]$

| | U11 | U22 | U33 | U23 | U13 | U12 |
|---|---|---|---|---|---|---|
| S(8) | 24(1) | 24(1) | 53(1) | -1(1) | -1(1) | 4(1) |
| O(1) | 24(2) | 23(2) | 24(2) | 3(2) | 0(2) | -2(2) |
| C(7) | 20(3) | 23(2) | 27(3) | -3(2) | -8(3) | 0(2) |
| F(3) | 55(2) | 88(3) | 42(2) | 15(2) | -16(2) | -13(2) |

TABLE 4-continued

Anisotropic displacement parameters (A^2 × 10^3) for 2003xf.
The anisotropic displacement factor exponent takes the form:
$-2\pi^2 [h^2 a^{*2} U11 + \ldots + 2 h k a^* b^* U12]$

| | U11 | U22 | U33 | U23 | U13 | U12 |
|---|---|---|---|---|---|---|
| N(4) | 19(2) | 14(2) | 31(3) | 3(2) | 3(2) | −3(3) |
| C(5) | 22(3) | 16(2) | 26(3) | −4(2) | 2(2) | 2(3) |
| F(2) | 69(3) | 53(2) | 39(2) | 5(2) | 29(2) | 3(2) |
| C(20) | 29(3) | 28(3) | 31(3) | −12(3) | −5(3) | −1(2) |
| F(1) | 61(2) | 35(2) | 46(2) | 5(2) | 5(2) | 5(2) |
| C(15) | 20(3) | 22(3) | 27(3) | 2(3) | −3(2) | 5(2) |
| C(6) | 23(3) | 17(2) | 33(3) | −1(2) | 11(3) | 1(2) |
| C(16) | 40(3) | 22(2) | 31(3) | −3(3) | 1(3) | −7(3) |
| C(10) | 20(3) | 30(3) | 27(3) | 2(3) | 8(3) | 4(3) |
| C(13) | 33(3) | 45(3) | 42(4) | 3(3) | 7(3) | 0(3) |
| C(9) | 20(3) | 38(3) | 31(4) | −8(3) | 2(3) | 7(3) |
| C(3) | 22(3) | 28(3) | 32(3) | 10(2) | 5(2) | 0(2) |
| C(12) | 22(3) | 29(2) | 41(4) | −1(3) | 8(3) | −7(3) |
| C(2) | 28(3) | 34(3) | 22(3) | −2(3) | 3(3) | 4(2) |
| C(21) | 27(4) | 50(4) | 43(4) | −16(3) | −1(3) | 10(3) |
| C(18) | 24(3) | 44(3) | 30(4) | −1(3) | 3(3) | 11(3) |
| C(17) | 42(4) | 26(3) | 40(4) | 0(3) | 9(3) | −6(2) |
| C(19) | 33(3) | 38(3) | 33(4) | −9(3) | 2(3) | 6(3) |
| C(11) | 20(3) | 49(4) | 52(4) | −18(3) | −3(3) | 8(3) |
| C(14) | 35(4) | 72(5) | 22(3) | 16(3) | −1(3) | −4(3) |
| Cl(1) | 24(1) | 16(1) | 46(1) | 1(1) | −1(1) | −1(1) |

X-Ray Crystallographic Data

TABLE 5

Hydrogen coordinates (×10^4) and isotropic displacement
parameters (A^2 × 10^3) for 2003xf.

| | x | y | z | U(eq) |
|---|---|---|---|---|
| H(7A) | 9558 | 1486 | 2630 | 30 |
| H(5A) | 11757 | −162 | 3392 | 26 |
| H(5B) | 12685 | 1877 | 3099 | 26 |
| H(20A) | 9954 | 420 | 1297 | 37 |
| H(6A) | 11398 | 4819 | 3611 | 29 |
| H(16A) | 11626 | 6536 | 2292 | 38 |
| H(13A) | 5919 | −637 | 3583 | 48 |
| H(3A) | 12902 | 1128 | 5645 | 33 |
| H(3B) | 11886 | −636 | 5043 | 33 |
| H(12A) | 4246 | −700 | 2387 | 37 |
| H(2A) | 10639 | 2529 | 5468 | 34 |
| H(2B) | 11575 | 4389 | 5085 | 34 |
| H(18A) | 12248 | 4302 | 5 | 40 |
| H(17A) | 12584 | 7087 | 1084 | 43 |
| H(19A) | 10941 | 1005 | 103 | 42 |
| H(11A) | 4354 | 1998 | 1248 | 50 |
| H(14A) | 7767 | 1799 | 3653 | 52 |
| H(4B) | 13680(60) | 2600(100) | 4430(30) | 53(19) |
| H(4A) | 13580(50) | 230(90) | 4400(30) | 29(17) |

X-Ray Crystallographic Data

TABLE 6

Torsion angles [deg] for 2003xf.

| | |
|---|---|
| C(9)—S(8)—C(7)—C(15) | 115.5(4) |
| C(9)—S(8)—C(7)—C(6) | −119.7(4) |
| C(3)—N(4)—C(5)—C(6) | 52.2(6) |
| C(19)—C(20)—C(15)—C(16) | −0.4(7) |
| C(19)—C(20)—C(15)—C(7) | 177.8(4) |
| C(6)—C(7)—C(15)—C(20) | 126.4(5) |
| S(8)—C(7)—C(15)—C(20) | −109.2(4) |
| C(6)—C(7)—C(15)—C(16) | −55.5(6) |

TABLE 6-continued

Torsion angles [deg] for 2003xf.

| | |
|---|---|
| S(8)—C(7)—C(15)—C(16) | 68.9(5) |
| C(2)—O(1)—C(6)—C(5) | 60.7(5) |
| C(2)—O(1)—C(6)—C(7) | −178.1(4) |
| N(4)—C(5)—C(6)—O(1) | −55.1(5) |
| N(4)—C(5)—C(6)—C(7) | −174.3(4) |
| C(15)—C(7)—C(6)—O(1) | −175.0(4) |
| S(8)—C(7)—C(6)—O(1) | 61.9(4) |
| C(15)—C(7)—C(6)—C(5) | −54.7(5) |
| S(8)—C(7)—C(6)—C(5) | −177.8(3) |
| C(20)—C(15)—C(16)—C(17) | 0.7(7) |
| C(7)—C(15)—C(16)—C(17) | −177.4(5) |
| C(11)—C(10)—C(9)—C(14) | 2.6(8) |
| C(21)—C(10)—C(9)—C(14) | −176.4(5) |
| C(11)—C(10)—C(9)—S(8) | −178.8(4) |
| C(21)—C(10)—C(9)—S(8) | 2.2(7) |
| C(7)—S(8)—C(9)—C(10) | −114.6(5) |
| C(7)—S(8)—C(9)—C(14) | 64.0(5) |
| C(5)—N(4)—C(3)—C(2) | −52.6(6) |
| C(14)—C(13)—C(12)—C(11) | −1.9(8) |
| C(6)—O(1)—C(2)—C(3) | −63.3(5) |
| N(4)—C(3)—C(2)—O(1) | 58.2(5) |
| C(9)—C(10)—C(21)—F(3) | −173.8(5) |
| C(11)—C(10)—C(21)—F(3) | 7.1(7) |
| C(9)—C(10)—C(21)—F(1) | −51.3(7) |
| C(11)—C(10)—C(21)—F(1) | 129.6(5) |
| C(9)—C(10)—C(21)—F(2) | 67.4(7) |
| C(11)—C(10)—C(21)—F(2) | −111.6(5) |
| C(19)—C(18)—C(17)—C(16) | 0.5(8) |
| C(15)—C(16)—C(17)—C(18) | −0.7(8) |
| C(17)—C(18)—C(19)—C(20) | −0.2(8) |
| C(15)—C(20)—C(19)—C(18) | 0.1(8) |
| C(9)—C(10)—C(11)—C(12) | −2.7(8) |
| C(21)—C(10)—C(11)—C(12) | 176.3(5) |
| C(13)—C(12)—C(11)—C(10) | 2.3(8) |
| C(12)—C(13)—C(14)—C(9) | 1.9(8) |
| C(10)—C(9)—C(14)—C(13) | −2.1(8) |
| S(8)—C(9)—C(14)—C(13) | 179.2(4) |

Symmetry transformations used to generate equivalent atoms

The invention claimed is:

1. A compound of formula (I)

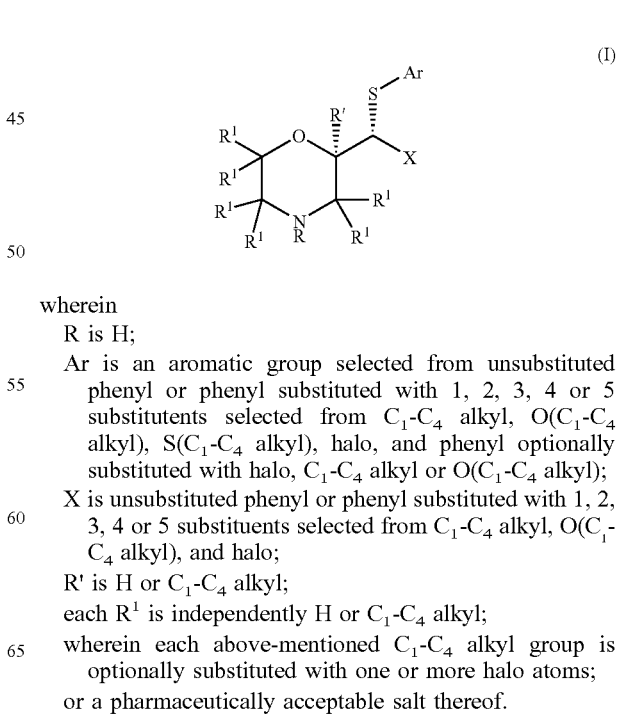

wherein
R is H;
Ar is an aromatic group selected from unsubstituted phenyl or phenyl substituted with 1, 2, 3, 4 or 5 substitutents selected from $C_1$-$C_4$ alkyl, O($C_1$-$C_4$ alkyl), S($C_1$-$C_4$ alkyl), halo, and phenyl optionally substituted with halo, $C_1$-$C_4$ alkyl or O($C_1$-$C_4$ alkyl);
X is unsubstituted phenyl or phenyl substituted with 1, 2, 3, 4 or 5 substituents selected from $C_1$-$C_4$ alkyl, O($C_1$-$C_4$ alkyl), and halo;
R' is H or $C_1$-$C_4$ alkyl;
each $R^1$ is independently H or $C_1$-$C_4$ alkyl;
wherein each above-mentioned $C_1$-$C_4$ alkyl group is optionally substituted with one or more halo atoms;
or a pharmaceutically acceptable salt thereof.

2. A compound as claimed in claim 1, represented by formula II:

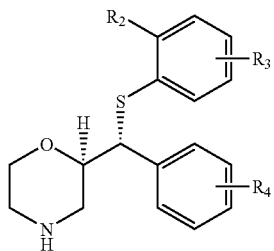

(II)

in which $R_2$ and $R_3$ are each independently selected from H, $C_1$-$C_4$ alkyl, O($C_1$-$C_4$ alkyl), S($C_1$-$C_4$ alkyl), halo, and phenyl; and $R_4$ is selected from H, $C_1$-$C_4$ alkyl, O($C_1$-$C_4$ alkyl) and halo;

wherein each above-mentioned $C_1$-$C_4$ alkyl group is optionally substituted with one or more halo atoms;

or a pharmaceutically acceptable salt thereof.

3. A compound as claimed in claim 2, wherein $R_2$ is selected from $C_1$-$C_2$ alkyl, O($C_1$-$C_2$ alkyl), S($C_1$-$C_2$ alkyl), Cl and F wherein each above-mentioned $C_1$-$C_2$ alkyl group is optionally substituted with one or more halo atoms.

4. A compound as claimed in claim 2 or claim 3, wherein $R_3$ is selected from H, Me and Cl.

5. A compound as claimed in claim 4, wherein $R_4$ is selected from H, $C_1$-$C_2$ alkyl, O($C_1$-$C_2$ alkyl), Cl and F wherein each above-mentioned $C_1$-$C_2$ alkyl group is optionally substituted with one or more halo atoms.

6. A composition comprising a compound as claimed in claim 1 or 2 together with a pharmaceutically acceptable diluent, excipient or carrier.

7. A method for treating persistent pain, comprising administering to a patient in need thereof an effective amount of a compound as claimed in claim 1.

* * * * *